US011020471B2

(12) United States Patent
Del Portillo Obando et al.

(10) Patent No.: US 11,020,471 B2
(45) Date of Patent: Jun. 1, 2021

(54) EXOSOMES AND THEIR USE AS VACCINE

(71) Applicants: INNOVEX THERAPEUTICS, S.L., Alella (ES); INSTITUCIÓ CATALANA DE RECERCA I ESTUDIS AVANÇATS, Barcelona (ES); FUNDACIÓ PRIVADA INSTITUTO DE SALUD GLOBAL BARCELONA (ISGLOBAL), Barcelona (ES); FUNDACIÓ INSTITUT D'INVESTIGACIÓ EN CIÈNCIES DE LA SALUT GERMANS TRIAS I PUJOL, Badalona (ES); UNIVERSITAT DE LLEIDA, Lleida (ES)

(72) Inventors: Hernando Antonio Del Portillo Obando, Alella (ES); Francisco Enrique Borrás Serres, Barcelona (ES); Lorenzo José Fraile Sauce, Lleida (ES); Sergio Roberto Montaner Tarbes, Barcelona (ES); Maria Montoya González, Madrid (ES)

(73) Assignees: INNOVEX THERAPEUTICS, S.L., Alella (ES); INSTITUCIÓ CATALANA DE RECERCA I ESTUDIS AVANCATS, Barcelona (ES); FUNDACIÓ PRIVADA INSTITUTO DE SALUD GLOBAL BARCELONA (ISGLOBAL), Barcelona (ES); FUNDACIÓ INSTITUT D'INVESTIGACIÓ EN CIÉNCIES DE LA SALUT GERMANS TRIAS I PUJOL, Badalona (ES); UNIVERSITAT DE LLEIDA, Lleida (ES)

( * ) Notice: Subject to any disclaimer, the term of this patent is extended or adjusted under 35 U.S.C. 154(b) by 0 days.

(21) Appl. No.: 15/579,153

(22) PCT Filed: Jun. 3, 2016

(86) PCT No.: PCT/EP2016/062637
§ 371 (c)(1),
(2) Date: Dec. 1, 2017

(87) PCT Pub. No.: WO2016/193422
PCT Pub. Date: Dec. 8, 2016

(65) Prior Publication Data

US 2018/0161416 A1 Jun. 14, 2018

(30) Foreign Application Priority Data

Jun. 3, 2015 (ES) .............................. ES201530775

(51) Int. Cl.
*A61K 39/12* (2006.01)
*A61K 38/17* (2006.01)
(Continued)

(52) U.S. Cl.
CPC ............. *A61K 39/12* (2013.01); *A61K 9/127* (2013.01); *A61K 38/1709* (2013.01);
(Continued)

(58) Field of Classification Search
None
See application file for complete search history.

(56) References Cited

U.S. PATENT DOCUMENTS

2018/0161416 A1* 6/2018 Del Portillo Obando .................. A61K 39/00

OTHER PUBLICATIONS

Anderson et al. (Neurotherapeutics. 2016; 13: 535-546).*

(Continued)

*Primary Examiner* — Shanon A. Foley
(74) *Attorney, Agent, or Firm* — Squire Patton Boggs (US) LLP

(57) ABSTRACT

The present invention provides exosomes isolated from an animal, wherein the animal (a) has overcome a disease
(Continued)

caused by a pathogen, and (b) it is free from the pathogen that causes the diseases. The invention also provides process for obtaining these exosomes and the use thereof in therapy.

16 Claims, 9 Drawing Sheets

Specification includes a Sequence Listing.

(51) Int. Cl.
*A61K 9/127* (2006.01)
*G06F 19/00* (2018.01)
*G16C 20/20* (2019.01)
*A61K 39/00* (2006.01)

(52) U.S. Cl.
CPC .............. *A61K 39/00* (2013.01); *G16C 20/20* (2019.02); *A61K 2039/55555* (2013.01); *A61K 2039/64* (2013.01); *C12N 2770/10034* (2013.01); *C12N 2770/10051* (2013.01); *C12N 2770/10071* (2013.01); *C12N 2770/36034* (2013.01); *C12N 2770/36051* (2013.01); *C12N 2770/36071* (2013.01)

(56) References Cited

OTHER PUBLICATIONS

Montaner-Tarbes et al. (Veterinary Research. 2016; 47: 59).*
Montaner-Tarbes et al. (Nature Scientific Reports. Nov. 2018; 8 (1): 17487).*
Wang et al. (Journal of Virology. Feb. 2018; 92 (4): 1-15).*
Montaner-Tarbes et al. (Frontiers in Veterinary Science. Feb. 2019; 6 (Article 38): 1-15).*
Pleet et al. (Frontiers in Microbiology. Nov. 2016; 7 (1765): 1-19).*
Pleet et al. (Viruses. 2019; 11 (410): 1-25).*
International Search Report and Written Opinion dated Nov. 2, 2016 for PCT/EP2016/062637, 15 pages.
Altschul, Stephen F., et al, "Basic local alignment search tool", 1990, Journal Molecular Biology, vol. 215, pp. 403-410.
Besse, Benjamin, et al., "Dendritic cell-derived exosomes as maintenance immunotherapy after first line chemotherapy in NSCLC", Aug. 12, 2015, Oncoimmunology, vol. 5, No. 4, pp. e1071008-1 through e1071008-13.
Boing, Anita N., et al., "Single-step isolation of extracellular vesicles by size-exclusion chromatography", Sep. 8, 2014, Journal of Extracell Vesicles, vol. 3, pp. 1-11.
Bradford, Marion M. "A rapid and sensitive method for the quantitation of microgram quantities of protein utilizing the principle of protein-dye binding", 1976, Analytical Biochemistry, vol. 72, pp. 248-254.
Chaput, Nathalie, et al. "Exosomes: immune properties and potential clinical implementations", Semin Immunopathol 2011, Dec. 21, 2010, vol. 33, pp. 419-440.
Charerntantanakul Wasin, "Porcine reproductive and respiratory syndrome virus Vaccines: immunogenicity, efficacy and safety aspects", Feb. 12, 2012, World Journal of Virology, vol. 1, Issue 1, pp. 23-30.
de Menezes-Neto, Armando, et al., "Size exclusion chromatography as a stand-alone methodology identifies novel markers in mass spectrometry analyses of plasma-derived vesicles from healthy indivuals", Journal of Extracellular Vesicles, Jul. 6, 2015, vol. 4, 27378, pp. 1-14.
De Toro, Julieta, et al., "Emerging Roles of Exosomes in Normal and Pathological Conditions: New Insights for Diagnosis and Therapeutic Applications", Frontiers in Immunology May 4, 2015, vol. 6, Article 203, pp. 1-12, doi:10.3389/fimmu.2015.00203, XP055293797.
Giri, Pramod K., et al., "Exosomes derived from *M. Bovis* BCG infected macrophages activate antigen-specific CD4+ and CD8+ T cells in vitro and in vivo", Jun. 18, 2000, Plos One, vol. 3, No. 6, pp. e2461.
Higgins, Desmond G., et al., "CLUSTAL V: improved software for multiple sequence alignment", 1992, CABIOS, vol. 8, No. 2, pp. 189-191.
Kalra, Hina, et al., "Comparative proteomics evaluation of plasma exosome isolation techniques and assessment of the stability of exosomes in normal human blood plasma", Proteomics Oct. 18, 2013, vol. 13, No. 22, pp. 3354-3364, doi:10.1002/pmic.201300282.
"Manual on meat inspection for developing countries", Food and Agriculture Organization of the United Nations Rome, 1994 (reprinted 2000), http://www.fao.org/docrep/003/t0756E00.htm#TOC, pp. 1-335.
Marcilla, Antonio, et al., "Extracellular vesicles in parasitic diseases", Dec. 22, 2014, Journal of Extracellular Vesicles, vol. 3, 25040, pp. 1-15.
Merrifield, R. B., "Solid phase synthesis. I. The synthesis of a tetrapeptide", J. Am Chem Soc., 1963, vol. 85, pp. 2149-2154.
Montaner-Tarbes, Sergio, et al., "Serum-derived exosomes from non-viremic animals previously exposed tothe porcine respiratory andreproductive virus contain antigenic viral proteins", May 31, 2016 Veterinary Research, vol. 47, No. 59, pp. 1-10, doi:10.1186/s13567-016-0345-x.
Raposo, Grace, et al., "B lymphocytes secrete antigen-presenting vesicles", J. Exp. Med., Mar. 1996, vol. 183, pp. 1161-1172.
Raposo, Grace, et al., "Extracellular vesicles: exosomes, microvesicles, and friends", Feb. 18, 2013, the Journal of Cell Biology, vol. 200, No. 4, pp. 373-383.
Schmitt, B., et al., "Diagnostic tools for animal diseases", Rev. Sci. Tech. Off. Int. Epiz., 2005, vol. 24, No. 1, pp. 243-250.
Schorey, Jeffrey S., et al., "Exosome function: from tumor immunology to pathogen biology", TRAFFIC Mar. 6, 2008, vol. 9, doi:doi:10.1111/j.1600-0854.2008.00734.x, pp. 871-881, XP002644382.
Théry, Clotilde, et al., "Membrane vesicles as conveyors of immune responses", Nat. Rev. Immunol., Aug. 2009, vol. 9, pp. 581-593.
Zhu, Li, et al., "Inhibition of porcine reproductive and respiratory syndrome virus infection by recombinant adenovirus- and/or exosome-delivered the artificial microRNAs targeting sialoadhesin and CD163 receptors", Virology Journal Dec. 19, 2014, vol. 11, No. 1, pp. 1-13, doi:10.1186/S12985-014-0225-9.
Zitvogel, L., et al., "Dendritic cells or their exosomes are effective biotherapies of cancer", European Journal of Cancer 1999, vol. 35, Supp. 3, pp. 36-38.
Egorov: "Universal influenza vaccine", Microbiology Independent Research Journal 2016, with English translation.
López-Soria, et al: "Effect of porcine circovirus type 2 (PCV2) load in serum on average daily weight gain during the postweaning period", Veterinary Microbiology 2014; vol. 174; pp. 296-301.
Lu: "Heterologous prime boost vaccination", Science Direct, Current Opinion in Immunology; Jun. 6, 2009; vol. 21; pp. 346-351.
Novikov: "Medical Immunology", Vitebskii Gosudarstvennyi Meditsinckii Universitet (Vitebsk State Medicine University); Approved by the Ministry of Education of the Republic of Belarus as a teaching aid for students of medical universities; VSMU Library 2002, with English translation.
Shulzhenko, et al: "Modern approaches to the diagnosis and treatment of herpesvirus infections", May 30, 2007, with English translation; downloaded from the internet Jun. 8, 2020 https://www.lvrach.ru/2007/05/4535200.
Snimshchikova, et al: "Aplasia of reticular tissue", Orlovskii Gosudarstvennyi Universitet (Orel State University), Medical Insitute, Department of Immunology and Specialized Clinical Disciplines; Course of lectures on applied immunology; Orel 2015; with English translation.
Wang, et al: "Long-term coexistence of SARS-CoV-2 with antibody response in COVID-19 patients", Journal of Medical Virology 2020; vol. 92; pp. 1684-1689.
Egorov: "Universal influenza vaccine", Microbiology Independent Research Journal 2016, vol. 3, No. 1., pp. 1-12; *abstract* pp. 2-3; with English translation.
Novikov: "Medical Immunology", Vitebskii Gosudarstvennyi Meditsinckii Universitet (Vitebsk State Medicine University); Approved by the Ministry of Education of the Republic of Belarus as a

(56) References Cited

OTHER PUBLICATIONS teaching aid for students of medical universities; VSMU Library 2002, vol. 235, pp. 18-19 with English translation.
Shulzhenko, et al: "Modern approaches to the diagnosis and treatment of herpesvirus infections", May 30, 2007, *the document in full*; with English translation; downloaded from the internet Jun. 8, 2020. https://www.lvrach.ru/2007/05/4535200.
Snimshchikova, et al: "Aplasia of reticular tissue", Orlovskii Gosudarstvennyi Universitet (Orel State University), Medical Insitute, Department of Immunology and Specialized Clinical Disciplines; Course of lectures on applied immunology; Orel 2015; pp. 73-76; with English translation.

* cited by examiner

EXOSOMES AND THEIR USE AS VACCINE

The present invention is related to animal health vaccines, more particularly it refers to exosomes isolated from an animal free of the pathogen that causes the disease, a process for its production, a pharmaceutical or veterinary composition comprising it and its use in the prevention or prophylaxis of infectious diseases, such as the one caused by the Porcine Reproductive and Respiratory syndrome virus (PRRSV).

BACKGROUND

Nowadays, there is an extensive research area in looking for alternative strategies to develop new vaccines that may solve many of current health problems. A new approach in this field is exosome-based vaccines (Chaput & Théry. Exosomes: immune properties and potential clinical implementations. 2011. Semi. Immunopathol., 33:419-440).

Exosomes are vesicles less than 300 nm in size, which are formed by fusion of cytoplasmic multivesicular bodies with the cellular membrane and their posterior release to the extracellular medium as extracellular vesicles. Initially, exosomes were described in tests performed with reticulocytes, precursor cells of erythrocytes. In those pioneer works, their biogenesis were elucidated, and it was proposed that they were plasma membrane-selective molecular waste derived from the differentiation process from reticulocytes to mature erythrocytes Ten years later, however, it was shown that exosomes were not unique of reticulocytes, being possible their production from other cell types and that they could have a modulating role in immune response (Raposo G. et al., "B lymphocytes secrete antigen-presenting vesicles", J. Exp. Med., 1996, vol. 183, pp. 1161-1172). Thus, Raposo and colleagues demonstrated in their works with B lymphocytes, that these cells also produced exosomes with the same physical and chemical properties as those disclosed for reticulocyte-derived exosomes. In addition, analysis of their molecular composition showed that exosomes from B lymphocytes contain class II histocompatibility complex proteins (MHCII) and that antigens could be presented to T lymphocytes when they were associated with them, eliciting antigen-specific immune responses. Since then, different studies have shown that exosomes can be secreted by almost all cell types, including cells of the immune system such as dendritic cells, macrophages and T and B lymphocytes. (Théry C. et al., "Membrane vesicles as conveyors of immune responses", Nat. Rev. Immunol., 2009, vol. 9, pp. 581-593). This discovery has opened the door to the use of these vesicles as a new therapeutic strategy in different diseases such as cancer. Thus, after finding that B lymphocytes were capable of producing exosomes with MHC-II class molecules and that they were capable of presenting the antigen to T lymphocytes, the same research group demonstrated three years later that dendritic cells (DCs), responsible of the generation of specific immunity, secreted exosomes with class I MHC molecules coupled to peptides which were capable of eliciting CD8 T-cytotoxic anti-tumor immune responses (Zitvogel L. et al., "Dendritic cells or their exosomes are effective biotherapies of cancer", European journal of cancer, 1999, vol. 35, Supl 3:S36-38). These pioneering studies set the molecular basis that exosomes acted in intercellular communication in the immune system and opened the door to the potential use of exosomes as new vaccines against tumors (Chaput & Théry. Exosomes: immune properties and potential clinical implementations. 2011. Semi. Immunopathol., 33:419-440). In fact, phase I clinical trials in patients with metastatic melanoma, lung cancer and colorectal cancer are currently ongoing as is mentioned in this review. Moreover, a Phase II clinical trial using dendritic cell-derived exosomes has recently been conducted in patients with non-small cell lung cancer (Besse et al., "Dendritic cell-derived exosomes as maintenance immunotherapy after first line chemotherapy in NSCLC", Oncoimmunology, 5(4): e1071008).

As in the cells of higher organisms, parasites and bacteria also secrete exosomes. Similarly, parasites and intracellular pathogens (including virus) promote exosome secretion by the host cell. In fact, in the last few years it has been demonstrated that such exosomes contain the "signature" of the pathogen in their molecular composition (Marcilla A. et al., "Extracellular vesicles in parasitic diseases", 2014, J Extracell. Vesicles 3, 25040, and Schorey J. S. & Bhatnagar S., "Exosome function: from tumor immunology to pathogen biology", 2008, Traffic, 9:871-81).

In view of the above, analysis of the potential use of exosomes as vaccines has increased in the past few years. The main advantages of using exosome-based vaccines against pathogens are: (i) pathogen-derived exosomes contain several naturally folded proteins of the pathogen; (ii) exosomes have wide biodistribution in the organism as they circulate in different body fluids reaching distant organs being protected from degradation and capable of traversing complex endothelial cell barriers such as the blood-brain barrier; (iii) there is a more efficient association with antigen presenting cells due to the presence of adhesins, among other molecules.

Some conceptual and practical aspects in the field of exosomes as prophylactic vaccines, however, need to be reviewed. One of them is that in all cases described so far, exosomes used as therapeutic agents have been isolated from samples of actively infected patients, animals or cell cultures. This represents an obstacle for their use as vaccine as it is cumbersome to demonstrate that these isolated exosomes are free of the pathogen which has caused the disease. For some pathogens, (specifically viral infections) this requirement is hard to accomplish because of the similar physico-chemical features (size and/or density) between the exosome produced and some of the pathogens causing the disease, such as the one caused by the Porcine Reproductive and Respiratory syndrome virus (PRRSV), thus requiring specific protocols for ensuring a pathogen-free exosome preparation are necessary. This step is not always possible and, when it is possible, the development of these specific protocols negatively affects both the cost and time needed in the manufacture of the vaccine.

In view of the above, there is the need of finding alternative strategies to those already available for the use of exosomes in the prevention and/or treatment of several pathologies.

DESCRIPTION OF THE INVENTION

The present inventors have found that an animal that has overcome a disease caused by a pathogen and that no longer shows pathogen trace, is capable of producing exosomes with a particular molecular signature of the pathogen. As shown in Example 5, liquid chromatography analysis coupled to mass spectrometry demonstrated that serum samples extracted from non-viremic animals which had already overcome the disease, contained exosomes displaying viral proteins.

This is a surprising result, taken into the account that, until now, there was the general thought that the active presence of the pathogen was needed to get exosomes derived from the organism including proteins and other pathogen-related biomolecules.

These findings represent a major advance in the field of vaccines. The fact that an organism, once has overcome a specific pathology caused by a pathogen, is capable of producing exosomes with potential immunogenic activity (due to the pathogenic protein profile expressed on their surface) without the active presence of the pathogen, can largely facilitate the manufacture of pathogen-free vaccines. In consequence, undesired secondary effects related to current vaccines, based on attenuated pathogens, are minimized.

In addition, the inventors have found that exosomes produced in the animal during infection and once overcome it, are different. As shown in FIGS. 2 and 3, an animal (swine) that has overcome a disease (Reproductive and Respiratory syndrome "PRRS") and that has no pathogen traces in plasma, as diagnosed by a sensitive and specific method, exhibit cysteine-protease c1ab/similar to papain, PRRSV uncharacterized putative protein, PRRSV polyprotein, NSP2, GP2b and ORF2a. In addition to the proteins identified in FIGS. 2 and 3, the envelope protein, the nucleocapsid protein, and ORF1a proteins have also been found to be differentially expressed (Example 10 below). These proteins are not detected in exosomes produced by swine during the infection.

Therefore, in a first aspect, the present invention provides an exosome isolated from an animal, wherein the animal (a) has overcome a disease caused by a pathogen, and (b) it is free from the pathogen causing the disease.

In the present invention, the expression "has overcome a disease" is understood as an animal that does not have any of the clinical signs which are characteristic of the disease and which were used at the time for diagnosing the disease. In one embodiment, the overcoming of the disease occurs naturally, i.e. by action of the immune system of the host against the pathogen, provided that the treatment is not an immunogen or vaccine.

Alternatively, in another embodiment, the overcoming of the disease occurs after administering a pharmacological treatment.

In the present invention, the expression "pathogen-free" and "no trace of pathogen" are interchangeably used and means that no pathogen load is detected in the sample taken from the animal. In an embodiment, the pathogen load is determined in a body fluid sample (such as plasma or serum). The protocols disclosed in the state of the art for diagnosing an animal disease, based on quantifying the pathogen, are also useful in the context of the present invention to evaluate if an animal is "pathogen-free". On the other hand, useful protocol(s) to determine the pathogen load for a particular pathogen are well established in the state of the art (Schimdt B. et al., "Diagnostic tools for animal diseases", Rev. Sci. Tech. Off. Int. Epiz., 2005, volum 24 (1), pages 243-250).

In the present invention, "pathogen" is understood as any agent capable of causing a disease or damage at some point to the host biology. In one embodiment, the pathogen is a microorganism. In another embodiment, the pathogen is a bacterium, fungus, virus or parasite.

In an embodiment of the first aspect of the invention, the animal has overcome a viral disease and it is free of the virus causing the disease.

In another embodiment of the first aspect of the invention, the animal has overcome a parasitic disease and it is free of the parasite causing the disease.

In another embodiment of the first aspect of the invention, the animal has overcome a bacterial disease and it is free of the bacterium causing the disease.

In one embodiment, the animal is a mammal. In another embodiment, the animal is a farm animal. As a non-limiting illustration, the term "farm animal" includes swine, cow, sheep and horse, among others. In an embodiment, the animal is a swine. Alternatively, in another embodiment, the animal is a human being.

Illustrative, non-limiting examples of virus, bacteria and parasites affecting farm animals are listed in the FAO document entitled "Manual on meat inspection for developing countries" of 1994 y re-published on 2000, chapters 3 to 8 (document available online on fao.org/docrep/003/t0756e/T0756E00 htm#TOC).

In another embodiment of the first aspect of the invention, the animal is a mammal that has overcome a viral disease and is free of the virus causing the disease (i.e., is a "non-viremic" animal).

In another embodiment of the first aspect of the invention, the animal is a farm animal that has overcome a viral disease and is free of the virus causing the disease.

In another embodiment of the first aspect of the invention, the animal is a swine that has overcome a viral disease and is free of the virus causing the disease.

In another embodiment of the first aspect of the invention, the animal is a swine that has overcome the Porcine Reproductive and Respiratory Syndrome (PRSS) and is free of the virus causing the disease.

The porcine reproductive and respiratory syndrome is characterized by defects in sow's reproduction and respiratory crisis in piglets and growing swines, being a significant cause of important economic losses. This syndrome is caused by a single stranded positive RNA virus (+ssRNA) with envelope and small size, classified in the order Nidovirales, family Arteriviridae and genus *Arterivirus*.

Until now, two types of vaccines have been developed against PRRSV, ones containing the dead virus and others, the latest ones, comprising attenuated virus with or without adjuvant. It has to be emphasized that the vast majority of these vaccines are only distributed in the countries where they are manufactured and that all of them need significant improvement in terms of efficacy and biosafety, especially in relation to obtaining a vaccine totally free of pathogen traces (CharerntantanakulW., "Porcine reproductive and respiratory syndrome virus Vaccines: immunogenicity, efficacy and safety aspects", 2012, World Journal of Virology, volume 1(1), pages 23-30). As has been mentioned above, with the exosomes of the invention, which are isolated from animals which have overcome the disease and are free of pathogen, a vaccine free of residual pathogen is obtained, thus improving vaccine biosafety.

The present invention means a great advance in the vaccine immunology field since it is the first time that it has been reported that pathogen-free animals, which have already overcome the disease, are capable of producing exosomes that are immunogenic, as shown below.

As it is shown in Example 7 and FIG. 4, the proteins identified in isolated exosomes are recognized by the immune sera of animals that have overcome infections, this being indicative of the immunogenic effect that exosomes of the invention can elicit.

In another embodiment of the first aspect of the invention, the animal is a mammal that has overcome a parasitic disease and is free of the parasite causing the disease.

In another embodiment of the first aspect of the invention, the animal is a farm animal that has overcome a parasitic disease and is free of the parasite causing the disease.

In another embodiment of the first aspect of the invention, the animal is a cow that has overcome a parasitic disease and is free of the parasite causing the disease.

In another embodiment of the first aspect of the invention, the animal is a cow that has overcome a parasitic disease, *Theileriosis*, and is free of the parasite causing the disease.

In another embodiment of the first aspect of the invention, the animal is a mammal that has overcome a bacterial disease and is free of the bacterium causing the disease.

In another embodiment of the first aspect of the invention, the animal is a farm animal that has overcome a bacterial disease and is free of the bacterium causing the disease.

In another embodiment of the first aspect of the invention, the animal is a swine that has overcome a bacterial disease and is free of the bacterium causing the disease.

In another embodiment of the first aspect of the invention, the animal is a swine that has overcome a bacterial disease, Mycoplasmosis, and is free of the bacterium causing the disease.

In a further effort, the inventors of the present invention have performed a proteomic analysis of the exosomes isolated from plasma samples either in PRRSV, Mycoplasmosis and *Theileriosis* infected animals and in animals which have overcome the disease and have no pathogen trace. From this analysis, peptide sequences SEQ ID NO: 1 to SEQ ID NO: 15 have been identified:

SEQ ID NO: 1
VEVEGHLMTSK

SEQ ID NO: 2
QAKKHEVAGANK

SEQ ID NO: 3
AGKKQSQK

SEQ ID NO: 4
NIAPMGNGQSVNQLCQLLGTMMK

SEQ ID NO: 5
MAGRNQRQK

SEQ ID NO: 6:
LEELFK

SEQ ID NO: 7:
KGSIVDIENQK

SEQ ID NO: 8:
MQIFVK

SEQ ID NO: 9:
TITLEVEPSDTIENVK

SEQ ID NO: 10:
IENLSDTFLSNNGKPEYKR

SEQ ID NO: 11:
AGFAGDDAPR

SEQ ID NO: 12:
IWHHTFYNELR

SEQ ID NO: 13:
YPIEHGIVTNWEDMEK

-continued

SEQ ID NO: 14:
STELLIRK

SEQ ID NO: 15:
EGDGVCTITAKMPKDEQK were found to be differentially comprised in exosomes from the group of swines which had overcome the disease, and were absent in swines with the infection.

In an embodiment of the first aspect of the invention, optionally in combination with any of the embodiments provided above or below, the exosome comprises a peptide comprising a sequence selected from the group consisting of: SEQ ID NO:1 to SEQ ID NO: 15, and a peptide sequence with an identity of at least 85% with any of the sequences SEQ ID NO: 1 to 15. In another embodiment of the first aspect of the invention, optionally in combination with any of the embodiments provided above or below, the exosome comprises a peptide comprising the sequence SEQ ID NO:1 or a sequence with an identity of at least 85% with SEQ ID NO: 1, and a peptide comprising the sequence SEQ ID NO: 2 or a sequence with an identity of at least 85% with SEQ ID NO: 2. In another embodiment of the first aspect of the invention, optionally in combination with any of the embodiments provided above or below, the exosome comprises a peptide comprising sequence SEQ ID NO:1 or a sequence with an identity of at least 85% with SEQ ID NO: 1, and a peptide comprising a sequence SEQ ID NO: 3, 4 or 5, or a sequence with an identity of at least 85% with SEQ ID NO: 3, 4 or 5, respectively. In another embodiment of the first aspect of the invention, optionally in combination with any of the embodiments provided above or below, the exosome comprises a peptide comprising sequence SEQ ID NO: 2 or a sequence with an identity of at least 85% with SEQ ID NO: 2, and a peptide comprising the sequence SEQ ID NO: 3, 4, or 5 or a sequence with an identity of at least 85% with SEQ ID NO: 3, 4, or 5. In another embodiment of the first aspect of the invention, optionally in combination with any of the embodiments provided above or below, the exosome comprises a peptide comprising the sequence SEQ ID NO: 1 or a sequence with an identity of at least 85% with SEQ ID NO: 1, a peptide comprising the sequence SEQ ID NO: 2 or a sequence with an identity of at least 85% with SEQ ID NO: 2, and a peptide comprising the sequence SEQ ID NO: 3, SEQ ID NO: 4, or SEQ ID NO: 5, or a sequence with an identity of at least 85% with SEQ ID NO: 3, 4, or 5, respectively. In another embodiment of the first aspect of the invention, optionally in combination with any of the embodiments provided above or below, the exosome comprises sequences SEQ ID NO: 1 to 5. In another embodiment of the first aspect of the invention, optionally in combination with any of the embodiments provided above or below, the exosome comprises a peptide comprising the sequence SEQ ID NO: 6 or a sequence with an identity of at least 85% and a peptide comprising the sequence SEQ ID NO: 7 or a sequence with an identity of at least 85%. In another embodiment of the first aspect of the invention, optionally in combination with any of the embodiments provided above or below, the exosome comprises a peptide comprising the sequence SEQ ID NO: 6 and a peptide comprising the sequence SEQ ID NO: 7. In another embodiment of the first aspect of the invention, the exosome comprises one or more peptides comprising a sequence selected from SEQ ID NO: 8 to SEQ ID NO: 15 or a sequence with an identity of at least 85% with any of the sequences SEQ ID NO: 8 to 15. In another embodiment of the first aspect of the invention, the exosome comprises a peptide comprising the sequence SEQ ID NO: 8 or a sequence having an identity of at least 85% with sequence SEQ ID NO: 8, a peptide comprising the sequence SEQ ID NO: 9 or a sequence having an identity of at least 85% with sequence SEQ ID NO: 9, a peptide comprising the sequence SEQ ID NO: 10 or a sequence having an identity of at least 85% with sequence SEQ ID NO: 10, a peptide comprising the sequence SEQ ID NO: 11 or a sequence having an identity of at least 85% with sequence SEQ ID NO: 11, a peptide comprising the sequence SEQ ID NO: 12 or a sequence having an identity of at least 85% with sequence SEQ ID NO: 12, a peptide comprising the sequence SEQ ID NO: 13 or a sequence having an identity of at least 85% with sequence SEQ ID NO: 13, a peptide comprising the sequence SEQ ID NO: 14 or a sequence having an identity of at least 85% with sequence SEQ ID NO: 14, and a peptide comprising the sequence SEQ ID NO: 15 or a sequence having an identity of at least 85% with sequence SEQ ID NO: 15. In another embodiment of the first aspect of the invention, the exosome comprises a peptide comprising the sequence SEQ ID NO: 8, a peptide comprising the sequence SEQ ID NO: 9, a peptide comprising the sequence SEQ ID NO: 10, a peptide comprising the sequence SEQ ID NO: 11, a peptide comprising the sequence SEQ ID NO: 12, a peptide comprising the sequence SEQ ID NO: 13, a peptide comprising the sequence SEQ ID NO: 14, and a peptide comprising the sequence SEQ ID NO: 15. The exosomes provided in these embodiments, wherein they comprise peptides comprising one or more peptides of sequence SEQ ID NO: 1 to 15, can alternatively be produced by routinely well-known techniques.

Thus, in a further aspect the present invention provides a vesicle comprising a peptide comprising a sequence selected from the group consisting of: SEQ ID NO:1 to SEQ ID NO: 15, and a peptide sequence with an identity of at least 85% with any of the sequences SEQ ID NO: 1 to 15. In an embodiment of this aspect optionally in combination with any of the embodiments provided above or below, the vesicle comprises a peptide comprising the sequence SEQ ID NO:1 or a sequence with an identity of at least 85% with SEQ ID NO: 1, and a peptide comprising the sequence SEQ ID NO: 2 or a sequence with an identity of at least 85% with SEQ ID NO: 2. In another embodiment of this aspect the invention, optionally in combination with any of the embodiments provided above or below, the vesicle comprises a peptide comprising sequence SEQ ID NO:1 or a sequence with an identity of at least 85% with SEQ ID NO: 1, and a peptide comprising a sequence SEQ ID NO: 3, 4 or 5, or a sequence with an identity of at least 85% with SEQ ID NO: 3, 4 or 5, respectively. In another embodiment of this aspect of the invention, optionally in combination with any of the embodiments provided above or below, the vesicle comprises a peptide comprising sequence SEQ ID NO: 2 or a sequence with an identity of at least 85% with SEQ ID NO: 2, and a peptide comprising the sequence SEQ ID NO: 3, 4, or 5 or a sequence with an identity of at least 85% with SEQ ID NO: 3, 4, or 5. In another embodiment of this aspect, optionally in combination with any of the embodiments provided above or below, the vesicle comprises a peptide comprising the sequence SEQ ID NO: 1 or a sequence with an identity of at least 85% with SEQ ID NO: 1, a peptide comprising the sequence SEQ ID NO: 2 or a sequence with an identity of at least 85% with SEQ ID NO: 2, and a peptide comprising the sequence SEQ ID NO: 3, SEQ ID NO: 4, or SEQ ID NO: 5, or a sequence with an identity of at least 85% with SEQ ID NO: 3, 4, or 5, respectively. In another embodiment of this aspect, optionally in combination with any of the embodiments provided above or below, the vesicle comprises sequences SEQ ID NO: 1 to 5. In another embodiment of this aspect, optionally in combination with any of the embodiments provided above or below, the vesicle comprises a peptide comprising the sequence SEQ ID NO: 6 or a sequence with an identity of at least 85% and a peptide comprising the sequence SEQ ID NO: 7 or a sequence with an identity of at least 85%. In another embodiment of this aspect of the invention, optionally in combination with any of the embodiments provided above or below, the vesicle comprises a peptide comprising the sequence SEQ ID NO: 6 and a peptide comprising the sequence SEQ ID NO: 7. In another embodiment of this aspect of the invention, the vesicle comprises one or more peptides comprising a sequence selected from SEQ ID NO: 8 to SEQ ID NO: 15 or a sequence with an identity of at least 85% with any of the sequences SEQ ID NO: 8 to 15. In another embodiment of this aspect of the invention, the vesicle comprises a peptide comprising the sequence SEQ ID NO: 8 or a sequence having an identity of at least 85% with sequence SEQ ID NO: 8, a peptide comprising the sequence SEQ ID NO: 9 or a sequence having an identity of at least 85% with sequence SEQ ID NO: 9, a peptide comprising the sequence SEQ ID NO: 10 or a sequence having an identity of at least 85% with sequence SEQ ID NO: 10, a peptide comprising the sequence SEQ ID NO: 11 or a sequence having an identity of at least 85% with sequence SEQ ID NO: 11, a peptide comprising the sequence SEQ ID NO: 12 or a sequence having an identity of at least 85% with sequence SEQ ID NO: 12, a peptide comprising the sequence SEQ ID NO: 13 or a sequence having an identity of at least 85% with sequence SEQ ID NO: 13, a peptide comprising the sequence SEQ ID NO: 14 or a sequence having an identity of at least 85% with sequence SEQ ID NO: 14, and a peptide comprising the sequence SEQ ID NO: 15 or a sequence having an identity of at least 85% with sequence SEQ ID NO: 15. In another embodiment of this aspect of the invention, the vesicle comprises a peptide comprising the sequence SEQ ID NO: 8, a peptide comprising the sequence SEQ ID NO: 9, a peptide comprising the sequence SEQ ID NO: 10, a peptide comprising the sequence SEQ ID NO: 11, a peptide comprising the sequence SEQ ID NO: 12, a peptide comprising the sequence SEQ ID NO: 13, a peptide comprising the sequence SEQ ID NO: 14, and a peptide comprising the sequence SEQ ID NO: 15.

In a second aspect, the present invention provides a peptide having a sequence length equal or lower than 100 amino acids and comprising a sequence selected from SEQ ID NO: 1 to 15 or a peptide sequence having at least 85% of identity with sequence SEQ ID NO: 1 to 15.

In the present invention the term "identity" refers to the percentage of residues or bases that are identical in the two sequences when the sequences are optimally aligned. If, in the optimal alignment, a position in a first sequence is occupied by the same amino acid residue or nucleotide as the corresponding position in the second sequence, the sequences exhibit identity with respect to that position. The level of identity between two sequences (or "percent sequence identity") is measured as a ratio of the number of identical positions shared by the sequences with respect to the size of the sequences (i.e., percent sequence identity=(number of identical positions/total number of positions)×100).

A number of mathematical algorithms for rapidly obtaining the optimal alignment and calculating identity between two or more sequences are known and incorporated into a number of available software programs. Examples of such programs include the MATCH-BOX, MULTAIN, GCG, FASTA, and ROBUST programs for amino acid sequence analysis, among others. Preferred software analysis programs include the ALIGN, CLUSTAL W, and BLAST programs (e.g., BLAST 2.1, BL2SEQ, and later versions thereof). For amino acid sequence analysis, a weight matrix, such as the BLOSUM matrixes (e.g., the BLOSUM45, BLOSUM50, BLOSUM62, and BLOSUM80 matrixes), Gonnet matrixes, or PAM matrixes (e.g., the PAM30, PAM70, PAM120, PAM160, PAM250, and PAM350 matrixes), are used in determining identity.

The BLAST programs provide analysis of at least two amino acid sequences, either by aligning a selected sequence against multiple sequences in a database (e.g., GenSeq), or, with BL2SEQ, between two selected sequences. BLAST programs are preferably modified by low complexity filtering programs such as the DUST or SEG programs, which are preferably integrated into the BLAST program operations. If gap existence costs (or gap scores) are used, the gap existence cost preferably is set between about −5 and −15. Similar gap parameters can be used with other programs as appropriate. The BLAST programs and principles underlying them are further described in, e.g., Altschul et al., "Basic local alignment search tool", 1990, J. Mol. Biol, v. 215, pages 403-410.

For multiple sequence analysis, the CULSTAL W program can be used. The CLUSTAL W program desirably is run using "dynamic" (versus "fast") settings. Amino acid sequences are evaluated using a variable set of BLOSUM matrixes depending on the level of identity between the sequences. The CLUSTAL W program and underlying principles of operation are further described in, e.g., Higgins et al., "CLUSTAL V: improved software for multiple sequence alignment", 1992, CABIOS, 8(2), pages 189-191.

In one embodiment of the second aspect of the invention, the peptide has a sequence length equal or lower than 50 amino acids. In another embodiment of the second aspect of the invention, the peptide is one of sequence SEQ ID NO: 16, 17, 18 or a sequence having at least 85% of identity with any of the sequences 6 to 8:

```
                                      SEQ ID NO: 16
LDAKGRLYRWRSPVIIEKGGKVEVEGHLMTSKELC (which
comprises sequence SEQ ID NO: 1)

                                      SEQ ID NO: 17
QAKKHEVAGANKAEHLKHYSPPAEGNCGWHCISAI (which
comprises sequence SEQ ID NO: 2)

                                      SEQ ID NO: 18
MAGRNQSQKKKKNIAPMGNGQSVNQLCQLLGTMMK
(which comprises sequences SEQ ID NO: 3-5)
```

Surprisingly, as it is shown below, peptides of sequence SEQ ID NO: 16 to 18 have immunogenic properties.

In view of the results provided below in Example 10, it can be concluded that the extracellular vesicle of the invention can be used as immunogen as such, but also as source for identifying peptides candidates to be immunogens of a particular disease. And the general methodology would be simple. An illustrative way of identifying immunogenic candidates would be to compare the proteomic analysis of an extracellular vesicle isolated from a subject suffering the disease with the one resulting from an exosome isolated from a subject that has successfully overcome the disease and has no pathogen trace, and those peptides that are differentially present can be selected as potential immunogen candidates. In particular, those peptides that are present in the extracellular vesicle of the invention and not in extracellular vesicle secreted during the infection are good candidates to be immunogenic.

In further embodiments, once the candidate has been identified, it can be tested to determine its effect in the immune system. But, alternatively, the skilled person in the art can opt for predicting the epitope sequence using free commercial softwares such as those listed in the IEDB Analysis Resource (tools.iedb.org), among which Bepipred can be used. Once the information about the epitope is achieved, the epitope can be synthesized using, for example, solid phase synthesis techniques (such as Fmoc) and tested to confirm the effect on the immune system.

In a third aspect, the present invention provides a process to obtain an extracellular vesicle according to the first aspect of the invention that comprises the separation of the extracellular vesicle from a test sample selected from a biological fluid or a tissue sample isolated from an animal that (a) has overcome a disease caused by a pathogen and (b) is free from the pathogen causing the disease.

The biological fluid can be serum, plasma, sweat, tears, milk or seminal fluid, among others.

The skilled person knows several techniques that can be used for separating exosome from other components contained in plasma. Illustrative not limitative examples include ultracentrifugation, filtration and size exclusion chromatography. The separation step referred in the process of the third aspect of the invention can comprise the use of one or more techniques, so that, for example, ultracentrifugation and subsequent size exclusion chromatography separation can be performed or, alternatively, it can be determined that only one technique is enough. In an embodiment of the third aspect of the invention, the separation is carried out using size exclusion chromatography. In another embodiment of the third aspect of the invention, the extracellular vesicle is an exosome and the separation is carried out using size exclusion chromatography through a Sepharose matrix.

In an embodiment of the third aspect of the invention, the process comprises, an exosome enrichment step of the sample such as precipitation with a polyglycol previous to the separation step. In another embodiment of the third aspect of the invention, the process comprises: (a) precipitate the isolated biological fluid sample with a polyglycol such as polyethylene glycol Mn6000 (8.5% weight/volume) with a final concentration of sodium chloride of 0.4M; (b) resuspend the resulting pellet of the mixing step (a) with a buffer; and (c) separate the exosomes from the suspension. The inventors have found that it is possible to scale up the process by carrying out a precipitation step with a polyol before the separation step, thus obtaining substantial amounts of exosomes. Step (a) can be carried out with any polyglycol, although in one embodiment the polyglycol is polyethylene glycol. Step (b) can be carried out with any buffer such as phosphate-buffered saline. In step (c) any of the techniques indicated previously for the separation of exosomes or a combination thereof (filtration, ultracentrifugation or size exclusion chromatography) can be used.

Alternatively, in a fourth aspect the present invention provides a process to obtain exosomes as defined in the first aspect of the invention that comprises the isolation and culture of reticulocytes from a blood sample collected from the animal and obtaining the exosome fraction derived from the reticulocytes. The reticulocyte-derived exosome fraction can be separated by ultracentrifugation, size exclusion chromatography or filtration. In an embodiment of the fourth aspect, the process comprises, previously to the exosome separation, an exosome enrichment step of the sample, such as precipitation with a polyglycol. In another embodiment of the fourth aspect of the invention, the process comprises: (a) reticulocyte isolation and culture from a blood sample taken from an animal (b) isolated biological fluid sample precipitation with a polyglycol, such as polyethilene glycol (8.5% weight/volume) at a final concentration of sodium chloride 0.4M; (c) resuspension of the pellet resulting from previous step (b) with a buffer; and (d) separate the exosomes in the suspension. Step (b) can be carried out with any polyglycol, although in one embodiment, the polyglycol is polyethylene glycol. Step (c) can be carried out with any buffer such as phosphate-buffered saline. In step (d) any technique for exosome isolation pointed out above can be used, either separately or in combination (filtration, ultracentrifugation or size exclusion chromatography).

In a fifth aspect, the present invention provides an extracellular vesicle obtainable by a process as defined in the second or third aspect of the invention.

The term "extracellular vesicle", such as "exosome" obtainable by the process is used herein for defining the extracellular vesicle by its preparation process and refers to the product that can be obtained through the preparation process which comprises the indicated steps as herein defined. For the purposes of the invention, the expressions "obtainable", "obtained" and similar equivalent expressions are used interchangeably and, in any case, the expression "obtainable" encompasses the expression "obtained".

From data shown in Example 7 and Example 10, it can be concluded that both the exosomes as well as the peptides of the invention have an immunogenic profile, being useful in therapy.

Thus, in a sixth aspect, the present invention provides a pharmaceutical or veterinary composition comprising an extracellular vesicle as defined in the first or fifth aspect, or a peptide as defined in the second aspect of the invention, and one or more pharmaceutically or veterinary acceptable excipients or carriers.

The term "pharmaceutically or veterinary acceptable" refers to excipients or carriers for their use in pharmaceutical or veterinary technology, in order to prepare compositions for medical use in humans or animals. Each component must be pharmaceutically or veterinary acceptable in the sense of being compatible with the other ingredients of the pharmaceutical or veterinary composition, respectively. It must also be suitable for use in contact with the tissue or organ of humans and animals without excessive toxicity, irritation, allergic response, immunogenicity or other problems or complications commensurate with a reasonable benefit/risk ratio.

In one embodiment of the sixth aspect, the present invention provides a composition comprising a therapeutically effective amount of the extracellular vesicle according to the first or fifth aspect of the invention, or the peptide as defined in the second aspect of the invention, and one or more pharmaceutically or veterinary acceptable excipients or carriers.

The expression "therapeutically effective amount" as it is used herein, refers to an amount of exosome or peptide that, when is administered, is sufficient to prevent the development or relieve to a certain extend of one or more symptoms of the disease. The specific dose of exosomes administered according to the invention will be determined for particular circumstances, such as the route of administration and the disease to be treated, among others.

Compositions of the present invention can be prepared using well-known methods in the state of the art. The skilled person in the art can determine the excipients and/or carriers, and suitable amounts to be used depending on the formulation to be prepared.

In an embodiment of the sixth aspect, the pharmaceutical or veterinary composition is a vaccine.

Excipients and adjuvants that can be incorporated to a vaccine are well-known by the skilled person in the art and will be selected, in such a way that they do not negatively affect the immunological activity of the exosome.

As indicate above, the isolated exosomes from swine that has overcome PRRSV syndrome have a suitable immunogenic profile, suggesting their use as a vaccine. The same conclusion can be derived from the experimental data provided for peptides isolated from exosomes of the invention (see Example 10). Thus, ELISA assays demonstrated that exosomes obtained from non-viremic animals used as coating antigens were specifically recognized by sera of animals previously exposed to the PRRSV virus and not from animals never infected. Moreover, immunization of naïve animals with exosomes obtained from non-viremic animals or with the peptides of the invention, as previously identified by mass spectrometry, demonstrated that they were able to elicit specific humoral and cellular immune responses.

Remarkably, animals that were primed with exosomes from non-viremic animals and boost with the synthetic peptides also elicit these responses unequivocally demonstrating that such exosomes contain and expose such proteins to the immune system of pigs. Last, as animals immunized with exosomes from non-viremic animals received 1 milligram of exosomes never develop PRRSV infection, this vaccination approach is free of virus.

Thus, advantageously, the vaccine of the present invention, comprising the extracellular vesicles or peptides of the previous aspects, is free of viral particles (avoiding the development of clinical symptoms and a possible pathogen spreading due to a reversion of virulence), and can be directly associated to the epidemiological context. In an illustrative but not limitative example, the vaccine can be associated to an epidemiological context in a farm and can be recognized by sera obtained from another farm with another epidemiological context (FIG. 4). Therefore, the vaccine will be capable of acting directly on the viral strain that is causing infection in diverse places and at a particular time.

In addition to the above, in Example 10 it is illustrated that the immune response raised, when the exosome or peptide or the invention is administered, triggers the production of protein markers different from those trigger during the infectious process.

Animal vaccination is the most important tool in the control and eradication of the diseases. However, current vaccines, based on the attenuated virus or dead virus stimulate an antibody response against the antigen very similar to that occurring during an infection. Since it has been established that the best diagnosis is based on detection of antibodies, it is no possible an accurate differentiation between vaccinated and infected animals.

The exosomes and peptides of the invention solves this problem providing a vaccine which would provide a "label" to the vaccinated animal such as the physician or veterinarian, depending on the subject, could easily determine whether the subject is suffering an infectious process or is vaccinated.

This differential protein pattern can help in differentiating vaccinated animals from infected animals.

Thus, in a seventh aspect the present invention provides the use of an extracellular vesicle as defined in the first or fifth aspect of the invention, for differentiating animals vaccinated with the vesicle as defined in the first or fifth aspect of the invention from the animals infected with the same pathogen as the one referred in the first aspect of the invention.

In addition to the above, in Example 10 it is illustrated that the immune response elicited in response to the pathogen and in response to the exosome of the invention are different.

As indicated before, the exosomes of the invention present an immunogenic profile, making it useful in treatment of diseases.

Therefore, in an eighth aspect, the present invention provides the use of an exosome or the peptide as it is defined in any of the previous aspects as an immunogen.

In an ninth aspect, the present invention provides the use of an exosome or peptide according to any of the previous aspects for use as a medicament.

In a tenth aspect, the invention provides the extracellular vesicle or peptide according to any of the previous aspects for use in the prevention or treatment of a viral, bacterial or parasitic disease. This aspect can also be formulated as the use of an extracellular vesicle or peptide according to any of the previous aspects for the manufacture of a medicament for the prevention or treatment of a viral, bacterial or parasitic disease. This aspect can be alternatively formulated as a method for the prevention or treatment of a viral, bacterial or parasitic disease, the method comprising the step of administering, to a subject in need thereof, a therapeutically effective amount of the extracellular vesicle or peptide defined in any of the aspects or embodiments of the present invention.

In one embodiment of the tenth aspect of the invention, the extracellular vesicle or peptide is used in the treatment or prevention of a disease selected from PRRSV, Mycoplasmosis and *Theileriosis* disease.

In an eleventh aspect, the present invention provides a method for identifying a peptide candidate to be an immunogen, the method comprising the step of analyzing the protein composition of the extracellular vesicle as defined in any of the above aspects.

The analysis of the protein composition of the exosome (quantitative proteomics) can be performed following any of the routine techniques, such as liquid chromatography and mass spectrometry (de Menezes-Neto et al., "Size exclusion chromatography as a stand-alone methodology identifies novel markers in mass spectrometry analyses of plasma-derived vesicles from healthy individuals, J. Extracell. Ves., 2015, 4: 27378).

In one embodiment of the eleventh aspect the present invention provides a method for identifying a peptide candidate to be an immunogen, the method comprising:

(a) analyzing the protein components of the extracellular vesicle, such as an exosome, as defined in the first or fifth aspect of the invention; and
(b) comparing the protein profile resulting from step (a) with the protein profile from an extracellular vesicle, such as an exosome, isolated from an animal suffering from the same disease as the animal from which the exosome used in step (a) is isolated;

wherein, if the peptide is included in the vesicle of the invention and not in the one from the infected animal is indicative of that peptide is candidate to be immunogen.

Throughout the description and claims the word "comprise" and variations of the word, are not intended to exclude other technical features, additives, components, or steps. Furthermore, the word "comprise" encompasses the case of "consisting of". Additional objects, advantages and features of the invention will become apparent to those skilled in the art upon examination of the description or may be learned by practice of the invention. The following examples and drawings are provided by way of illustration, and they are not intended to be limiting of the present invention. Reference signs related to drawings and placed in parentheses in a claim, are solely for attempting to increase the intelligibility of the claim, and shall not be construed as limiting the scope of the claim. Furthermore, the present invention covers all possible combinations of particular and preferred embodiments described herein.

Figure 1:
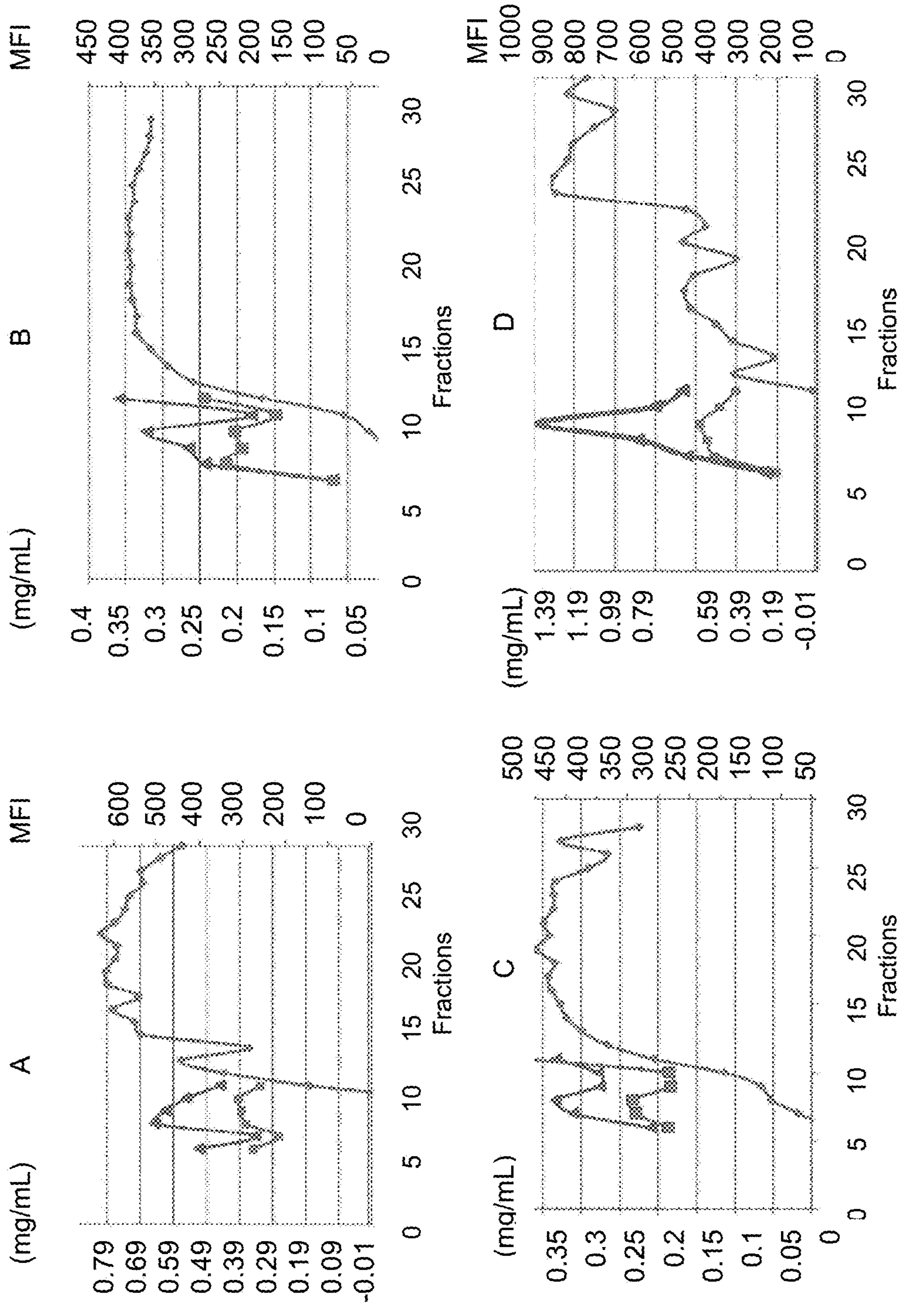
FIG. 1. Protein elution profile analysis using Bradford assay and marker analysis CD63 (b) and CD81 (c) using flow cytometry. In the figure, Bradford (mg/mL) and median fluorescence (MFI) patterns for each of the samples tested was observed. It is remarkable the high values of fluorescence previously to elution of soluble protein in the process of size exclusion chromatography fractions. These MFI values allow differentiation of those enriched-vesicle fractions from those containing a large amount of soluble protein (not associated to vesicles). A and B correspond to samples of viremic animals (201406-2PS and 201406-4PS); C and D correspond to samples from non viremic pigs (201406-6PS and 201406-10PS).

In both cases, fraction 8 represents the most enriched fraction in molecular markers associated to exosomes. CD63 and CD81 are used as guide for selecting fractions to be send to proteomic analyses.

EXAMPLES

1. Sample Collection.

Sera samples from farm animals in which there had been an episode of PRRSV were collected. To determine which samples belonged to animals that had overcome the disease, the Group Porcine Sanitation (GSP—Grup de Sane-jament Porci) of Lleida conducted blind analyses of these samples by techniques: (i) RT-PCR which detects the active virus RNA indicating that serum belongs to a viremic animal (Taqman PRRSV reagents and controls), and (ii) ELISA to detect antibody titers using a commercial kit (IDEXX PRRS X3 Ab test). Notably, the GSP group is accredited in Catalonia for diagnosis of this pathogen (gspl-leida.net/ca/content/laboratori).

In parallel, animal sera samples were collected in farms in Lleida where there had not been reported, until today, any PRRSV episode. These sera were evaluated using the same tests in the GSP. In this group, the samples that were negative both in RT-PCR (that means absence of the active virus) and in ELISA (which means, that there was no infection ongoing), were considered as negative controls.

From the results obtained, two samples of viremic animals (referred to hereinafter as 201406-2PS and 201406-4PS) and two non-viremic animals (201406-6PS and 201406-10PS) were selected.

Example 2. Serum-Derived Exosome Isolation

The exosomes have a characteristic particle size of 30-100 nm. Therefore, to collect these vesicles from different samples a separation process through size exclusion chromatography using sepharose CL2B as separation matrix, was used (de Menezes-Neto et al., "Size exclusion chromatography as a stand-alone methodology identifies novel markers in mass spectrometry analyses of plasma-derived vesicles from healthy individuals, J. Extracell. Ves., 2015, 4: 27378). While there are other techniques for preparing exosomes, the sepharose technique allows a better purification of the exosomes. Briefly, frozen 3 mL aliquots of different sera samples were thawed on ice and centrifuged at 500 g for 10 minutes at room temperature to disregard cell debris. In parallel, sepharose CL-2B (Sigma-Aldrich, St. Louis, Mo., USA) were packed in 12 mL syringes until a final volume of 10 mL, and balanced with phosphate-buffered saline (PBS) 0.32% of sodium citrate (w/v). Later, 2 mL aliquots of each sample were added to individual sepharose CL-2B columns and 18-20 fractions of 0.5 mL aliquots were collected for each sample.

Example 3. Molecular Characterization of Exosomes

Once obtained the different exosome fractions, the presence of the vesicles was confirmed by the analysis of protein concentration using Bradford assay, and the analysis using molecular markers performed by flow cytometry.

3.1. Bradford Analysis.

Protein concentration was obtained using a colorimetric assay with Bradford technique (Bradford M. M. "A rapid and sensitive method for the quantitation of microgram quantities of protein utilizing the principle of protein-dye binding", 1976, Analytical biochemistry, vol. 7(72), päginas 248-254)

3.2. Flow Cytometry.

In parallel, fractions were also analyzed by flow cytometry to detect the presence of the antigens CD9, CD63 or CD81, two tetraspanins that are particular exosome markers (Raposo G. et al., "Extracellular vesicles: exosomes, microvesicles, and friends", 2013, The Journal of cell biology, vol. 18(200), page 373-383). Each aliquot was subjected to the following protocol: 4 microns of latex beads (aldehyde-sulfate) (Invitrogen Cat° A37304) were added to each aliquot, and the mix was left for 15 minutes in resting conditions before adding 1 mL of BCB buffer (PBS×1, 0.1% bovine serum albumin, 0.01% of sodium azide). The resulting mix was incubated overnight at room temperature in rotation before the incubation with primary antibodies (anti-CD63 and anti-CD81, kindly provided by Dr. Francisco Sanchez-Madrid) for 30 minutes at 4° C. Both antibodies were used in 1:10 dilution. After two wash steps with 150 μL of PBS-BSA buffer (Phosphate-buffered saline/bovine serum albumin 0.1%), and centrifugation at 2000 g for 10 minutes, secondary antibodies conjugated to FITC (1:100 dilution) or alexa 488 (1:1000 dillution) (Southern Biotec cat° 1032-02) were added and the mix was incubated for 30 minutes at 4° C. After two additional wash steps with 150 μL of PBS-BSA buffer at 0.1% at 2000 g for 10 minutes, the latex beads were resuspended in 100 μL of PBS-BSA 0.1%.

Resulting samples were analyzed by flow cytometry using LRSFortessa flow cytometer (BD Biosciences) and adjusting counting threshold at 10000 events. Using FlowJo analysis software, FCS files corresponding to each sample processed were added to the worklist, the area (forward and side scatter) where latex beads population was concentrated was selected, and the fluorescence for FITC related to this area was measured. A table was made with the median intensity fluorescence (MFI) data and bead counts obtained in the gated area for each sample analyzed. 20000 individual latex beads were examined per sample and the MFI was used for comparison between fractions.

Following both protocols, as shown in FIG. 1, it was possible to identify the exosome containing fractions from those containing soluble protein, verifying, additionally, that viremic and non-viremic samples had a similar elution pattern: it was detected an increase in fluorescence signal for CD63 and CD81 molecular markers just before Bradford analysis started to detect soluble protein in analyzed fractions.

Example 4. Exosome Protein Profile Analysis 4.1. Analysis of the Distribution and Size of the Exosomes Using Nanoparticle Tracking Analysis (NTA).

The use of NTA for quantification, distribution and size of exosomes, has become one of the most used techniques in the extracellular vesicles field. (malvern.com/en/products/technoloy/nanoarticle-tracking-analysis/). Therefore, after the confirmation of the presence of the markers associated to these vesicles in the fractions, the inventors decided to quantify the number and the size of the vesicles population present in the analyzed samples. In order to do so, each analyzed sample was diluted in PBS until the NTA chamber (Malvern Instruments Ltd) detected a value between 20-100 particles per field. Once reached this ideal concentration and dilution, 400 μL were injected into the NTA chamber and microscope capture level was manually adjusted. The digital thermometer was activated and the focalization of the particles with less refraction was started using the micrometer of the microscope in the area closest to the laser beam circumferences. Automatic acquisition of videos was started, and the analysis of the obtained videos was done using the software developed by the equipment's supplier. Thus, it was confirmed that the majority of samples had a vesicle concentration in order of magnitude of 1010 particles per milliliter. In addition, mode size was measured and ranged between 40-150 nm.

4.2. Protein Electrophoresis.

Figure 2:
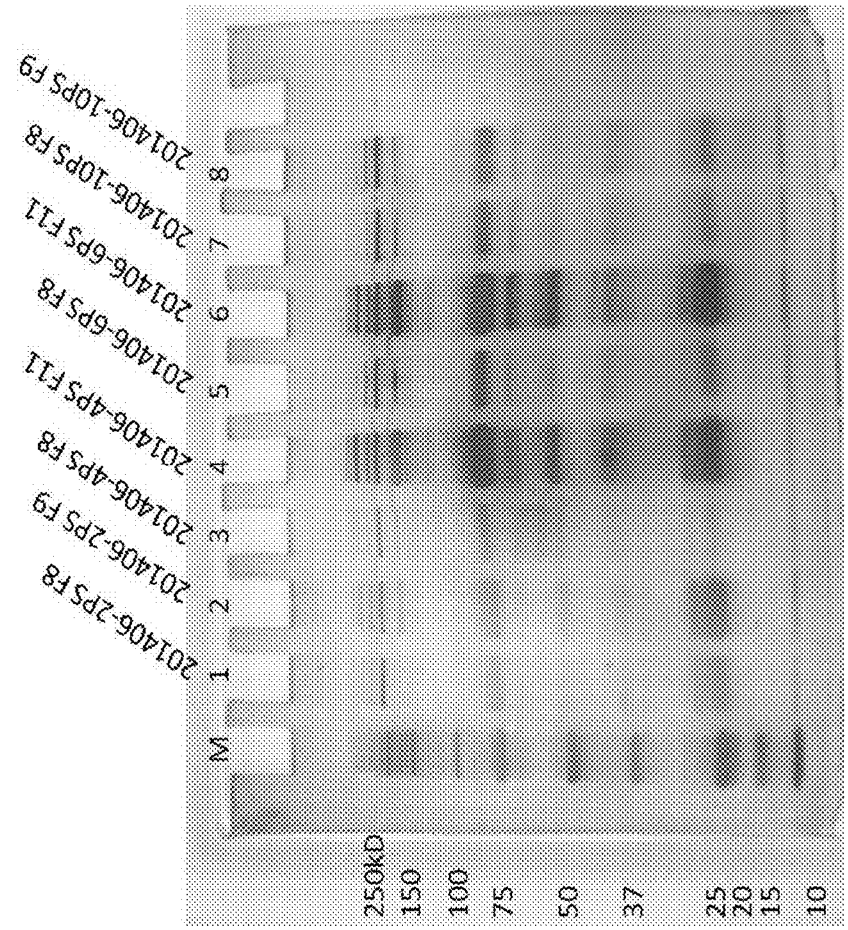
FIG. 2. Protein polyacrylamide gel electrophoresis in reducing conditions. (M) Molecular weight marker in Kilo-Daltons. Protein pattern obtained for different fractions of four analyzed samples. Two viremic swines (2PS and 4PS) and two swines that has overcome the disease (6PS and 10PS)

In order to detect the presence of exosomal and eluted proteins in the exosome-enriched fractions and determine their molecular weight range, all selected fractions were analyzed using electrophoresis in reducing conditions and silver staining process. In order to do this, two aliquots of 10 μL of each fraction collected in example 1 were taken, and 10 μL of cracking buffer (Bio-Rad) were added to each one. Then, each sample was loaded into a pre-cast 10% SDS-PAGE gel (Bio-Rad). FIG. 2 shows obtained results. From the electrophoretic result, it could be concluded that protein composition in viremic and non-viremic samples was different. For example, non-viremic samples presented a protein band of approximately 15 kDa that was absent in viremic samples. Nevertheless, in order to show unequivocally that the molecular composition of exosomes isolated from animals that had overcome the disease was different from those obtained from viremic animals, we proceed to the proteomic characterization by liquid chromatography-Mass spectrometry.

Example 5. Proteomic Analysis Using Liquid Chromatography And Mass Spectrometry Liquid chromatography (nanoLCULTRA-EKSIGENT) followed by mass spectrometry (LC-MS/MS) was carried out in an LTQ Orbitrap Velos equipment (Thermo Fisher). Exosome samples in PBS, were reduced with 10 mM DTT (Dithiothreitol), alkylated with 55 mM of iodoacetamide, and precipitated with 10% trichloroacetic acid (TCA), washed with 100% acetone and reconstituted in 2 mL of 8M urea. Before overnight digestion with trypsin, samples were resuspended in 1.6M urea solution. Reaction was stopped with 1% formic acid (v/v) and trypsinized samples were passed through a precolumn (C18PepMap-100-Thermoscientific-5 mm-ID300 um-5 um-100 A), before their injection in an analytical column (AcclaimPepMap100-Thermoscientific-15 cm-ID75 um-3 um-100 A-C18). Samples eluted at 400 nL/minute with a mobile phase gradient: 0-40% of dissolvent B in dissolvent A for the first 80-90 minutes and then 40-100% of dissolvent B in dissolvent A until experiment ending at 100-110 minutes (A: 3% acetonitrile, 0.1% formic acid in water, B: 97% acetonitrile, 0.1% formic acid in water). The Eluate was applied to the nano-spray source of the spectrometer Orbitrap and all full-scan mass spectra acquired in the Orbitrap over a mass range of 400-1500 m/z with a resolution of 30,000 and a maximum injection time of 500 ms were analyzed. The MS/MS was done in the LTQ and the 20 more intense peptides were isolated and fragmented using a low collision energy 35% CID. Maxquant v1.5 software was used to analyze the raw data, using the label-free-quantification (LFQ) mode. Moreover, for the final identification we used the sequence search engine, Andromeda (module included in Maxquant v1.5 software), adding a sequence dataset created from the sequences obtained from the UniProtKB website, including all PRRSV proteins sequences that had been sequenced until that moment (approximately 14000 sequences).

Figure 3:
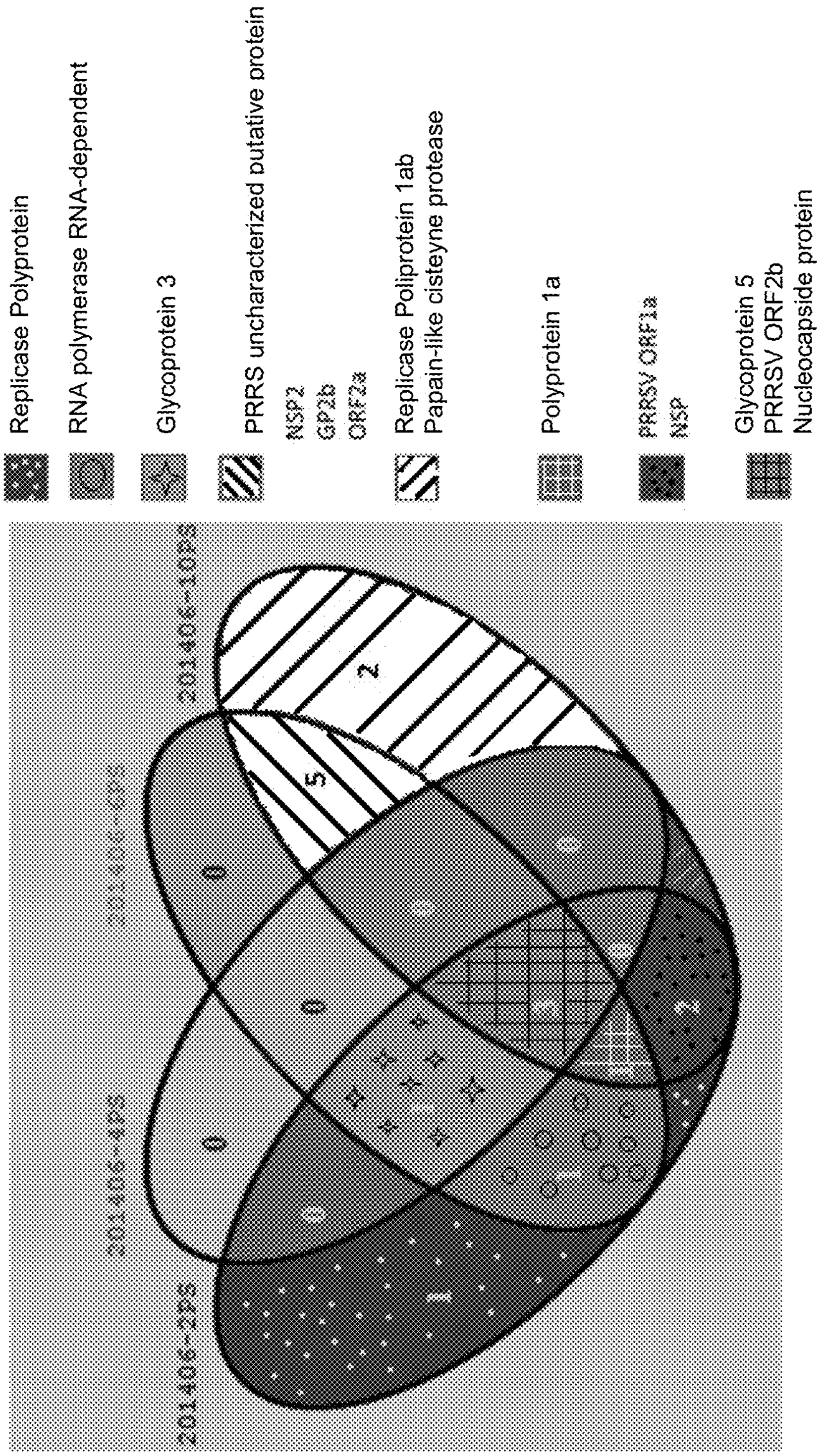
FIG. 3. Venn diagram to compare protein diversity of Porcine Respiratory and Reproductive Syndrome virus (PRRSV) in animal samples from viremic (201406-2PS/201406-4PS) and animals that have overcome the viral infection (201406-6PS/201406-10PS)
Figure 4:
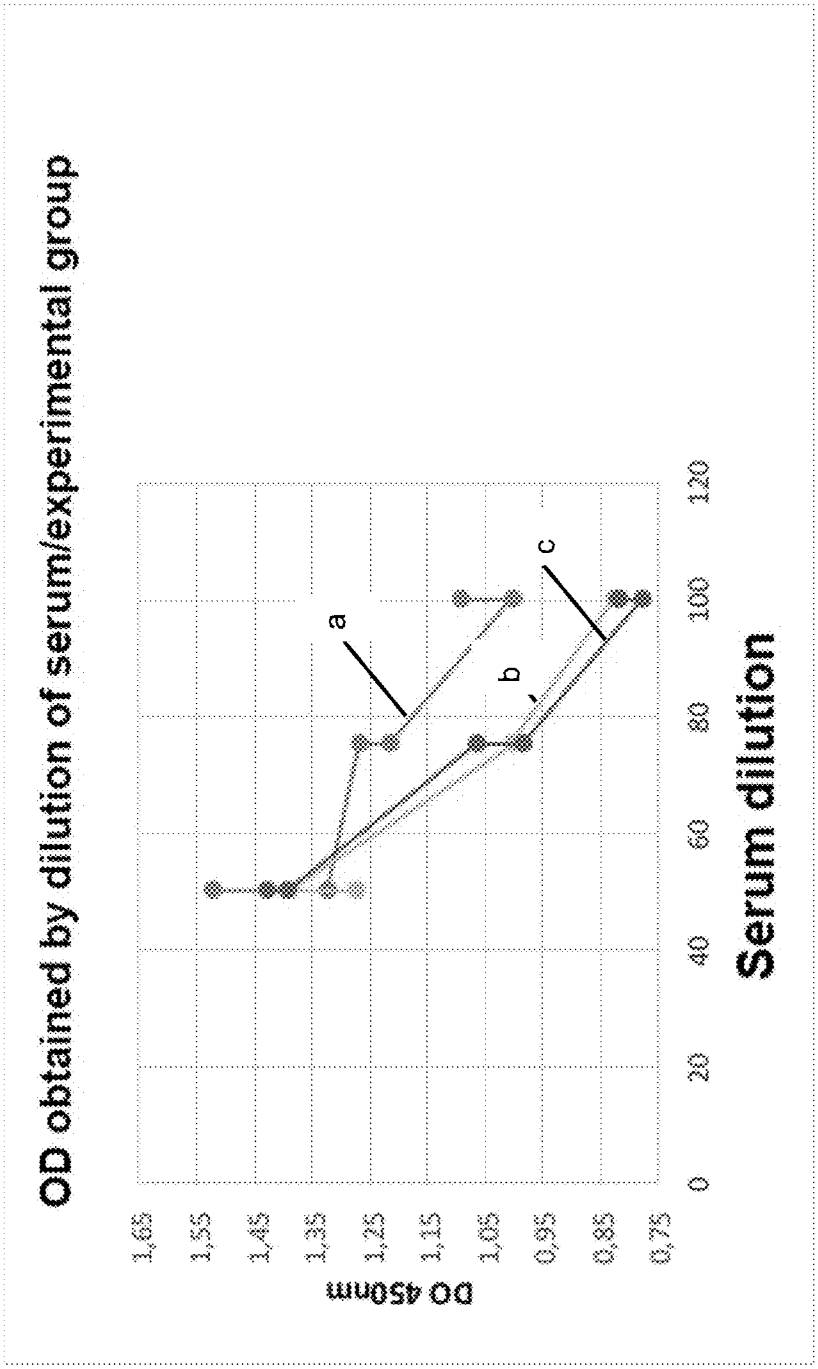
FIG. 4. Optical density (OD) results at 450 nm derived from a sandwich-type ELISA (CAPTURE ELISA) where sera from animals that have overcome the infection are evaluated. (a) non-viremic swine+non-viremic sera (b) Naïve swine+non-viremic sera and (c) Human reticulocyte-derived exosomes+non-viremic sera.

From this analysis, a variety of viral proteins was identified in all samples. Surprisingly, as it is shown in the Venn diagram of FIG. 3, the present inventors have found that molecular composition of exosomes produced in the animal during or after the overcome of the infection are different. Thus, it could be concluded that exosomes produced in an animal (swine), which has overcome the disease (Reproductive and respiratory Syndrome virus "PRRSV"), and that does not present traces of the pathogen in plasma (201406-6PS and 201406-10PS), expresses the proteins: replicase polyprotein 1ab/papain-like cistein protease, putative uncharacterized protein PRRSV, PRRSV polyprotein, NSP2, GP2b, ORF2a, that are not present in exosomes produced by the animal during acute infection (201406-4PS and 201406-2PS). Importantly, all proteins identified by Maxquant v1.5 have an associated probability known as PEP or posterior error probability, which indicates the probability to misidentify one protein by comparison. All the proteins identified in this analysis presented a PEP<0.0001, reinforcing the validity of these results.

Example 6. Isolation of Exosomes from Human Reticulocyte Cells

For reticulocyte isolation, anticoagulated blood extracted from healthy human donors at sufficient volume to ensure a high yield for this technique was used. Blood was transferred to 50 mL tubes and centrifuged 15 minutes at 1000 g, ACC 8/DEC 3 to separate plasma (liquid) from cells (solid). Plasma was discarded and globular package (cells) was diluted at 50% hematocrit with RPMI 1640 media and centrifuged for 10 minutes at 600 g, ACC 8/DEC 3, the supernatant was discarded and cells were resuspended again in RPMI 1640 to achieve a 50% hematocrit. An aliquot was taken to evaluate the initial cell concentration of the sample (reticulocyte represent approximately 2% of total cell count).

To eliminate white cell population (leukocytes) from the dilution, the globular package at 50% hematocrit was passed through a CF11 column (Whatman, 4021050) so that leukocytes were retained in the matrix due to their size, and red cells (group where reticulocytes can be found) passed through the matrix, and were collected in 15 mL falcon tubes.

Collected volume (eluted from the CF11 column) including all red cells was examined by direct vision to detect blood clots and, if found, sample was passed through a nylon filter. Then, the sample was centrifuged 10 minutes at 600 g, ACC8/DEC 3, the supernatant was discarded, and the pellet was resuspended until a 50% hematocrit.

For reticulocyte enrichment, it was used a Percoll separation. To do so, addition of Percoll (GE Healthcare, 17-0891-02), prepared (Percoll Stock: 9 parts of pure Percoll and 1 part of 1.5M sodium chloride-Percoll separation solution: 70% Percoll stock and 30% sodium chloride 0.15M), to 15 mL falcon tubes was done and, afterwards, the sample was shed onto the walls of the tube, so that the reticulocytes were applied at the upper part of the tube. Another centrifugation step was done at 1200 g/15 min/ACC 4/DEC 0, thus, reticulocytes were separated by density from the mature red blood cells, and formed a ring in the middle of the tube. Finally, reticulocyte rings were collected directly from the percoll gradient tubes, transferred to 15 mL falcon tubes, and washed two-three times by addition of RPMI 1640 media up to the maximum volume (15 mL) to eliminate percoll traces with centrifugations for 7 minutes at 500 g between each media wash step. Blood smears were done both with Brilliant cresyl blue (Sigma) and giemsa stain (Sigma) from the samples obtained with this method in the initial point (direct sample), posterior to leukocyte depletion with CF11 (Sigma) and after percoll enrichment. This guaranteed the correct performance of all processes and that the reproducibility criteria followed the quality controls.

In addition, reticulocyte cell suspension was cultured in cell culture flasks with RPMI 1640 culture media without supplementation for 36 hours. Exosomes were isolated from the cell culture supernatant following the protocols described in example 2.

Example 7. Immunogenicity of Viral Proteins Associated to Exosomes 7.1. ELISA Protocol for Antibody Titration.

Indirect ELISA protocol was used for sera titration obtained from swine that had overcome PRRSV infection (PCR (−); Ab (+), "NV"), those with detectable viremic state (PCR (+); Ab (+/−), "V") and those that never had been in contact with the virus (PCR (−); Anb (−), "CN"). General protocol for indirect ELISA was described by Abcam Company. Briefly, a coating with the antigen of interest corresponding to attenuated PRRSV vaccine available in the market (Porcilis PRRS Vaccine "intervet" lot. A200ED03) was done onto flat bottom microtiter polyvinylchloride (PVC) plate. Stock dilution of the antigen was done using carbonate/bicarbonate buffer ($Na_2CO_3$ 0.015M/$NaHCO_3$ 0.035M) at pH 9.6 until reaching normal dose concentration for vaccination in swine. In each well 50 μL of the dilution of the antigen was loaded and incubated overnight at 4° C. with a plastic cover to avoid evaporation. At the end of the antigen incubation step, the remaining volume in the wells was discarded by inversion and 4 plate washes were done with 200 μL PBS 1×/Tween 20 0.2%. Once the plate was washed, a blocking step was carried out, to fill the empty spaces where the antigen had not bind to in order to avoid unspecific results of the assay, by the addition of PBS 1×/5% non-fat dry milk. After blocking, the plate was washed four times with PBS 1×/Tween 20 0.2%, and the different sera groups were incubated (NV, V and CN, diluted from 1/5 to 1/5000) for 1 hour at room temperature, followed by four washes with PBS 1×/0.2% Tween 20. Finally, the plate was incubated with secondary antibody goat anti-pig (Fc): HRP (AbSerotec, AAI41P) in dilutions from 1/100 to 1/100000 for 1 hour at room temperature and light protected. Four posterior washes with PBS 1×/0.2% Tween 20 were done.

ELISA reaction development was carried out using TMB substrate (3,3,5,5-Tetramethilbenzidine) from Abcam (Ab142042) following manufacturer instructions (15-20 minutes of development), and reaction was stopped adding 2M sulfuric acid. The ELISA results were read with Varioskan from Thermo-Scientific at 450 nm. The same protocol was followed in posterior examples to determine the optic density of the fraction in each well.

As seen in the results obtained from different sera groups and antibodies in the above mentioned assay, it was concluded that best sera dilutions to see differences between experimental groups (NV, V and CN) were between 1/50 to 1/100 combined with a secondary antibody dilution of 1/10000. This combination of factors was taken as standard for later assays where antigen recognition capacity by the sera from the different experimental groups had to be evaluated.

7.2. Recognition of Exosome Associated Viral Proteins Derived from Swine that had Overcome the Infection.

The coating with the antigen of interest corresponding to attenuated viral vaccine available in the market for PRRSV (Porcilis PRRS Vaccine "intervet" lot. A200ED03) was done onto a part of a flat bottom microtiter PVC plate, the other part of the plate was coated with a 1/10 dilution of the antibody mouse anti-human CD63 clone TEA 3/18 (kindly provided by Dr. Francisco Sanchez-Madrid). Antigen stock was diluted in carbonate/bicarbonate buffer ($Na_2CO_3$ 0.015M/$NaHCO_3$ 0.035M) pH 9.6 until reaching vaccination dose, and 1/10 for capture antibody. In each well of the ELISA plate, 50 μL of the dilution of antigen/capture antibody was loaded and incubated overnight at 4° C. covered with an adhesive plastic cover to avoid evaporation. At the end of the antigen incubation step (coating), the remaining volume in the wells was discarded by inversion and 4 plate washes were done with 200 μL PBS 1×/Tween 20 0.2%. Once the plate was washed, a blocking step was done to block empty spaces where the antigen had not bind to in order to avoid unspecific results of the assay, by the addition of 100 μL PBS 1×/5% non-fat dry milk. After blocking, the plate was washed four times with PBS 1×/Tween 20 0.2%, and the capture wells were incubated for 90 minutes at 37°C with 100 μL of extracellular vesicles obtained from animals that overcome the PRRSV infection (isolated by polyethylene glycol (Sigma-Aldrich Cat° 81260-1 KG)), and, as a specificity control, with exosomes derived from human reticulocytes, as PRRS is a pathogen specific for swine, these were obtained according to example 6. All exosomes were obtained by size exclusion chromatography using CL-2B sepharose matrix (Sigma-Aldrich cat° CL2B300-100ML).

Those wells in which commercial vaccine was added (used as positive control), were covered with 100 μL PBS 1× to maintain a minimal volume in the well to avoid protein damage due to desiccation. Then, each well was washed four times with 200 μL of PBS 1×/tween 20 0.2%. Afterwards, the plate was incubated with the different sera (NV, V and CN, diluted 1/25 to 1/100) for 1 hour at room temperature, followed by four washes with PBS 1×/Tween 20 0.2% (v/v). Finally, the plate was incubated with the secondary antibody goat anti-pig (Fc): HRP (AbSerotec, AAI41P) at 1/10000 dilution for 1 hour at room temperature and light protected with four posterior washes with PBS 1×/0.2% tween 20. ELISA reaction development was carried out using TMB substrate (3,3,5,5-Tetramethilbenzidine) from Abcam (Ab142042) following manufacturer instructions (15-20 minutes of development), and reaction was stopped adding 2M sulfuric acid ($H_2SO_4$). Plate was read in Varioskan (Thermo-Scientific) at 450 nm.

The results obtained in the sandwich ELISA, indicated that the optical densities obtained from the vesicles derived from animals that had overcome PRRSV infection were significantly (p=0.02) higher than those derived from animals that had not been in contact with the virus (negative control), and those derived from human reticulocytes (specificity control).

By comparing these two controls with the experimental group, it can be observed a trend of antigen-antibody recognition specificity comparing Nv sera and Pigex Nv, that is not present in the two controls (NC, negative control and REX, specificity).

Example 8. Scalability Process and Production of Exosomes Derived from Swine that has Overcome PRRSV Infection First, the total volume of sera obtained by separation through centrifugation of total blood samples, collected directly on the farm, from animals that had overcome PRRSV infection (identified in example 1) was measured. Once total volume of sera was quantified, concentration was achieved by addition of polyethylene glycol "PEG" (Sigma-Aldrich cat 81260) at 8.5% (w/v and sodium chloride (Sigma-Aldrich cat° S5150-1 L) up to a final concentration of 0.4M. The mix was incubated overnight in a cold chamber (4° C.) under agitation. After this incubation, the mix was centrifuged using a high-speed centrifuge at 7000 g for 10 minutes and 4° C. Supernatant was discarded and the pellet was resuspended in PBS 1×.

The resulting suspension was aliquoted in 1.5 mL Eppendorf tubes and stored at −80° C. until use. A 2 mL aliquot was used to proceed with the exosome separation by size exclusion chromatography (SEC).

The column to perform the separation by the above-mentioned method was done using a 10 mL syringe (BD™ disposable syringe cat° BD302188), in which the tip was filled with a nylon cap to avoid sepharose matrix elution while compacting, and an opening/close valve to control the flux of eluate being filtered through the column. Once the opening/closing system was prepared, CL-2B sepharose matrix (Sigma-aldrich CL2B300-100ML) was loaded into the column until 10 mL of compacted sepharose matrix was reached. When the column preparation was finished, it was exposed to ultraviolet light for 10 minutes in a laminar flow hood. Meanwhile, 1.5 mL Eppendorf collection tubes for fraction collection were prepared and labeled with sample code, processing date and fraction number. Then, the 2 mL sample obtained by PEG concentration was loaded into the column and separation was done by the collection of approximately 0.5 mL fractions and supplementing the column with PBS 1×/0.32% sodium citrate to avoid matrix desiccation. After the collection of the 20 fractions of 0.5 mL, the valve was closed and fractions were analyzed by Bradford assay to quantify the protein concentration in each fraction.

After protein quantification by Bradford, a protein concentration profile was obtained. This profile had a detectable and quantifiable protein peak in those fractions were vesicles were enriched (a light increase in fractions 6 to 10), decreased after those fractions, and increased in a second peak corresponding to soluble protein elution fractions. Soluble proteins are smaller than vesicles, and thus, they have a delayed elution time in the size exclusion chromatography. This Bradford profile allows the determination of the vaccine dose unit that could be used in clinical trials and the expression of it with quantification Bradford units (mg/mL).

Example 9. Scalability Process (Using Differential Centrifugation Enrichment) and Production of Exosomes Derived from Swine that has Naturally Cured from PRRSV First, blood samples obtained from animals that naturally cured from PRRSV infection were centrifuged at 1800 rpm/15 minutes (Beckman Coulter Allegra X-12R centrifuge), sera was collected (identified in example 1) and volume measured. Extracellular vesicles were separated from cell debris by centrifugation at 500 g for 15 minutes in 50 mL falcon tubes. Supernatant was kept and pellet discarded. A second centrifugation in Beckman Coulter Optima XL-100K Ultracentrige (Rotor SW-28, class CDFGH, Ser. 5E 1427) for microvesicles and apoptotic bodies elimination at 15000 g for 45 minutes was carried out in polypropylene tubes (Beckman Coulter Ref. 326823—Lot. Z51002SCA). Supernatant was kept and pellet was discarded. Finally, to precipitate extracellular vesicles and soluble protein was necessary a ultracentrifugation step (Beckman Coulter Optima XL-100K Ultracentrige and Rotor SW-28, class CDFGH, Ser. 5E 1427) at 100000 g for 2 hours in polypropylene tubes, in this case, supernatant was discarded and pellet was resuspended in PBS 1×.

The resulting suspension was aliquoted in 1.5 mL Eppendorf tubes and stored at −80° C. until use. For size exclusion chromatography separation, 2 mL of the previous suspension was thawed and loaded into the separation column. The size exclusion column was done using a 10 mL syringe (BD™ disposable syringe cat° BD302188), in which the tip was filled with a nylon cap to avoid matrix elution while packaging and also an opening/close valve to control the flux of eluate through the column. Once prepared the opening/closing system, added CL-2B sepharose matrix (Sigma-Aldrich CL2B300-100ML) until 10 mL of packaged sepharose matrix was loaded into the column. When packaging process was finished, the column was moved into a laminar flow hood and exposed to ultraviolet light for 10 minutes in the meantime while 1.5 mL Eppendorf collection tubes for fractions were prepared and labeled with sample code, processing date and fraction number. Then, 2 mL of concentrated sample obtained from differential centrifugation method was loaded into the column and separation procedure started collecting 0.5 mL fractions approximately and loading PBS 1×/0.32% sodium citrate to avoid matrix desiccation. After 20-fraction collection, the opening/close valve was closed and fractions were analyzed by Bradford assay to quantify concentration of proteins within each fraction.

After protein quantification by Bradford, a protein concentration profile was obtained for each sample. This profile had a detectable and quantifiable protein peak in those fractions were vesicles were enriched (a light increase in fractions 6 to 10), decreased after those fractions, and increased in a second peak corresponding to soluble protein elution fractions. Soluble proteins are smaller than vesicles, and thus, they have a delayed elution time in the size exclusion chromatography. This Bradford profile allows determining the vaccine dose unit that could be used in clinical trials and express it as the quantification Bradford unit (mg/mL).

Example 10

10.1. Animals Used for Exosome Isolation, Characterization and Vaccine Production.

Sera samples for exosome isolation, molecular characterization and vaccine production were obtained from animals that had overcome PRRSV infection as judged (i) by RT-PCR (TaqMan® NA and EU PRRSV Reagents and Controls) to detect circulating viral particles in blood and (ii) by antibody detection post-infection (IDEXX PRRS X3 Ab test). An independent diagnostics laboratory for porcine diseases in Lleida, Grup de Sanejament Porci of Lleida (GSP), performed these analyses following their own standard operational procedures. Among all the animals evaluated and registered under test result number UP1570743, three were selected for further analyses and vaccine production (Table 1).

TABLE 1

| ANIMAL SERA INFORMATION FOR VACCINE PREPARATION. | | | | |
|---|---|---|---|---|
| ID number | ID from Farm | Aptitude | RT-PCR | Antibody titer |
| 201506-1PS | 1 | Male | — | 2.5 |
| 201506-6PS | 6 | Male | — | 2 |
| 201506-9PS | 9 | Male | — | 2.1 |

10.2. Proteomic Analysis Using Liquid Chromatography and Mass Spectrometry.

Liquid chromatography (nanoLCULTRA-EKSIGENT) followed by mass spectrometry (LC-MS/MS) was carried out in a LTQ Orbitrap Velos equipment (Thermo Fisher). Exosome samples in PBS 1× were reduced with 10 mM DTT (Dithiothreitol), alkylated with 55 mM of iodoacetamide and precipitated with 10% trichloroacetic acid (TCA), washed with 100% acetone and reconstituted in 2 mL of 8M urea. Before overnight digestion with trypsin, samples were resuspended in 1.6M urea solution. After complete overnight digestion, reaction was stopped with 1% formic acid (v/v) and trypsinized samples were passed through a precolumn (C18PepMap-100-Thermoscientific-5 mm-ID300 um-5 um-100 A) before injection in an analytical column (AcclaimPepMap100-Thermoscientific-15 cm-ID75 um-3 um-100 A-C18). Samples eluted at 400 nL/minute with a mobile phase gradient: 0-40% of dissolvent B in dissolvent A for the first 80-90 minutes and then 40-100% of dissolvent B in dissolvent A until experiment ending at 100-110 minutes (A: 3% acetonitrile, 0.1% formic acid in water, B: 97% acetonitrile, 0.1% formic acid in water). Eluate was applied to the nano-spray source of the spectrometer Orbitrap, and all full-scan mass spectra acquired in the Orbitrap over a mass range of 400-1500 m/z with a resolution of 30,000 and a maximum injection time of 500 ms were analyzed.

The MS/MS was done in the LTQ and the 20 more intense peptides were isolated and fragmented using a low collision energy 35% CID. Maxquant v1.5 software was used to analyze the raw data, using the label-free-quantification (LFQ) mode. Moreover, for the final identification we used the sequence search engine, Andromeda (module included in Maxquant v1.5 software), adding a sequence dataset created from the sequences obtained from the UniProtKB website, including all PRRSV proteins sequences that had been sequenced until that moment (approximately 14000 sequences). Contaminants were filtered out and peptides were considered true-positives if they fulfill the following criteria: (i) False-discovery-rate (FDR)=1%, (ii) more than two peptides from the same protein were identified in individual samples or a unique peptide was identified, (iii) it had to be present in exosomes from at least two different animals.

TABLE 2

| SEQUENCES IDENTIFIED BY LC-MS/MS AND SELECTED BY ANTIGENICITY. | | |
|---|---|---|
| SEQ ID NO: 1 | Peptides (LC-MS/MS) | Protein |
| 1 | VEVEGHLMTSK | Envelope protein |
| 2 | QAKKHEVAGANK | ORF1a polyprotein |

TABLE 2-continued

| SEQUENCES IDENTIFIED BY LC-MS/MS AND SELECTED BY ANTIGENICITY. | | |
|---|---|---|
| SEQ ID NO: 1 | Peptides (LC-MS/MS) | Protein |
| 3 | AGKKQSQK | Nucleocapsid protein |
| 4 | NIAPMGNGQSVNQLCQLLGTMMK | Nucleocapsid protein |
| 5 | MAGRNQRQK | Nucleocapsid Protein |

10.3. Epitope Prediction and Mapping

Protein sequences were evaluated using Bepipred 2.0 (iedb.org/). Bepipred 2.0 predicts the location of linear B-cell epitopes using a combination of a hidden Markov model and a propensity scale method. The residues with scores above the threshold (default 0.35) are predicted to be part of an epitope and colored gray in the graph (where Y-axes depicts residue scores and X-axes residue positions in the sequence). The values of the scores are not affected by the selected threshold. Peptides identified by MS/MS (Table 2) were then localized to determine whether they mapped in predicted B-cell epitope regions.

TABLE 3

| PREDICTED EPITOPE SEQUENCES FROM BEPIPRED 2.0 | |
|---|---|
| SEQ ID NO: | |
| 16 | LDAKGRLYRWRSPVIIEKGGKVEVEGHLMTSKELC |
| 17 | QAKKHEVAGANKAEHLKHYSPPAEGNCGWHCISAI |
| 18 | MAGRNQSQKKKKNIAPMGNGQSVNQLCQLLGTMMK |

10.4. Synthetic Peptides

After signing a confidentiality agreement with the "Peptide synthesis facility of the Department of Experimental and Health Sciences" at University Pompeu Fabra (Barcelona—Spain), peptides were synthesized using Fmoc chemistry Merrifield R. B. Solid phase synthesis. I. The synthesis of a tetrapeptide, J. Am Chem Soc., 1963, vol. 85, p. 2149-2154). Thus, peptide chains were assembled stepwise, one amino acid at a time, while attached to an insoluble resin support. This allowed the reaction by-products to be removed at each step by simple washing. Amino acids were protected at their amino terminus by the Fmoc (9-fluorenylmethoxycarbonyl) group and coupled to the growing chain after activation of the carboxylic acid terminus. The Fmoc group was removed by piperidine treatment and the process repeated. After the peptide was assembled, it was removed from the resin by treatment with trifluoroacetic acid (TFA). At the same time, protecting groups on amino acid side chains were also removed yielding the crude linear peptide. One-step purification by reverse-phase HPLC sufficed to obtain peptide with >95% purity.

Characterization of each synthetic peptide was done using an A-HPLC with a Column Luna C18 (4.6×50 mm, 3 um; Phenomenex), a Gradient: Linear B (0.036% TFA in MeCN) into A (0.045% TFA in $H_2O$) over 15 minutes with a flow rate of 1 mL/min and detection at 220 nm. All peptides were resuspended in ultrapure $H_2O$ (MiliQ water), aliquoted and stored at −20° C. until use.

10.5. Farm Vaccination Trial

Figure 5:
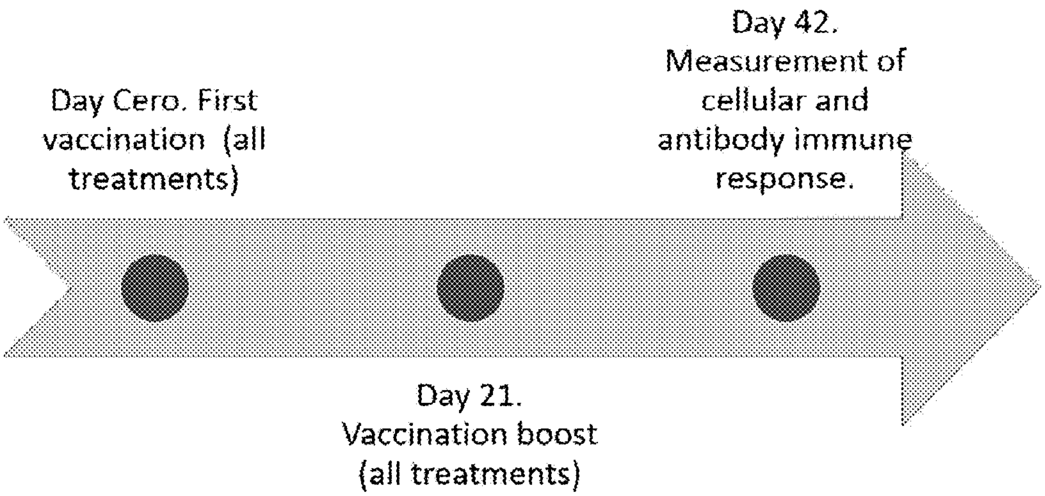
FIG. 5 represents a scheme and chronogram of the farm trail performed in Example 10.

To determine the immunogenicity of these peptides as well as of exosomes containing them, a porcine vaccine trial was performed at the experimental farm animal facilities of the University of Lleida (FIG. 5). The studies were approved by the ethical committee of the University of Lleida, Spain, and performed under their guidelines for animal care (DAAM7684). Control sera was defined as sample collected at day zero of each animal (pre-immune sera—Naïve animals).

Table 4 shows the experimental groups tested in the vaccination trial. All the animals used in the vaccination trial were in the same environment.

TABLE 4

ANIMAL DISTRIBUTION IN FARM AND VACCINATION TREATMENT IN FARM TRIAL.

| Left ear number | Experimental group |
|---|---|
| 87 | 1 mg Exosomes NV + Montanide |
| 90 | 1 mg Exosomes NV + Montanide |
| 86 | 1 mg each peptide + montanide |
| 85 | 1 mg each peptide + montanide |
| 81 | 1 mg each peptide + montanide |

"each peptide" means peptide of sequence SEQ ID NO: 16, 17, and 18

The adjuvant used for the vaccination trial was Montanide ISA 206 VG (SEPPIC—Lot. 36022E/U42131). MONTANIDE™ ISA 206 VG is a mineral oil based adjuvant, which has been developed for the manufacture of Water-in-Oil-in-Water (W/O/W) emulsions. It comprises a high-grade injectable mineral oil and an extremely refined emulsifier obtained from mannitol and purified oleic acid of vegetable origin. MONTANIDE™ ISA 206 VG is free of animal origin ingredients. Vaccine formulations with it induces short and long-term immunity.

Compared to traditional oil emulsions, MONTANIDE™ ISA 206 VG emulsions are stable, with low viscosity and easy to inject. It has been demonstrated that it is an excellent adjuvant to stimulate humoral and cellular responses. This product is recommended for bacterial, *mycoplasma*, viral or parasite antigens. Montanide™ adjuvants and their components have been considered as safe by the Committee for Veterinary Medical Products (CVMP) for use in immunological products and are included as authorized substances in the annex of the European Council Regulation n° 470/2009 (previously 2377/90/EC) needing no further MRL studies, or included in already registered veterinary commercial products. The recommended ratio for vaccine dose is 1:1 Montanide/vaccine antigen (weight/weight).

10.6. Immunogenicity of Peptides and Exosomes

Indirect ELISA was used to determine the immunogenicity of the different vaccine formulations. Briefly, flat bottom microtiter polyvinylchloride (PVC) plates were coated with 50 μL of the attenuated PRRSV vaccine (Porcilis PRRS Vaccine "intervet" lot. A200ED03) or peptides, a final concentration of 5 μg/mL in carbonate/bicarbonate buffer was prepared ($Na_2CO_3$ 0.015M/$NaHCO_3$ 0.035M), as coating antigens. Vaccines samples were diluted in carbonate/bicarbonate buffer to an approximate concentration corresponding to a normal vaccine dose indicated on the vaccine protocol ($10^4$ to $10^6$ $TCID_{50}$ for Porcilis PRRSV).

Stock dilutions of the antigens were done using carbonate/bicarbonate buffer ($Na_2CO_3$ 0.015M/$NaHCO_3$ 0.035M) at pH 9.6. In each well 50 μL of the dilution, either of Porcilis or peptides, were loaded and incubated overnight at 40° C. with a plastic cover to avoid evaporation. Then, coating solutions were discarded and plates were washed 4 times with 200 μL PBS 1×/0.2% Tween 20. After washing, a blocking step with PBS 1×/5% non-fat dry milk was necessary to cover all empty spaces without antigen in well surfaces to avoid unspecific binding. Four washing steps with PBS 1×/0.2% Tween 20 were carried out and incubation with different sera groups diluted 1/50 in PBS 1×/0.2% Tween 20 (from the immunization assay) for 1 hour at room temperature, followed by four washing steps with PBS 1×/0.2% Tween 20. Secondary antibody goat anti-pig (Fc): HRP (AbSerotec, AAI41P) was used as detection antibody at dilution 1/10000 for 1 hour at room temperature and light protected after which four washing steps with PBS 1×/0.2% Tween 20 were applied. ELISA development was carried out using TMB substrate (3,3,5,5-Tetramethilbenzidine) from Abcam (Ab142042) following manufacturer instructions (15-20 minutes of development), and reaction was stopped adding 2M sulfuric acid ($H_2SO_4$). Plate was read in Varioskan (Thermo-Scientific) at 450 nm.

Figure 6:
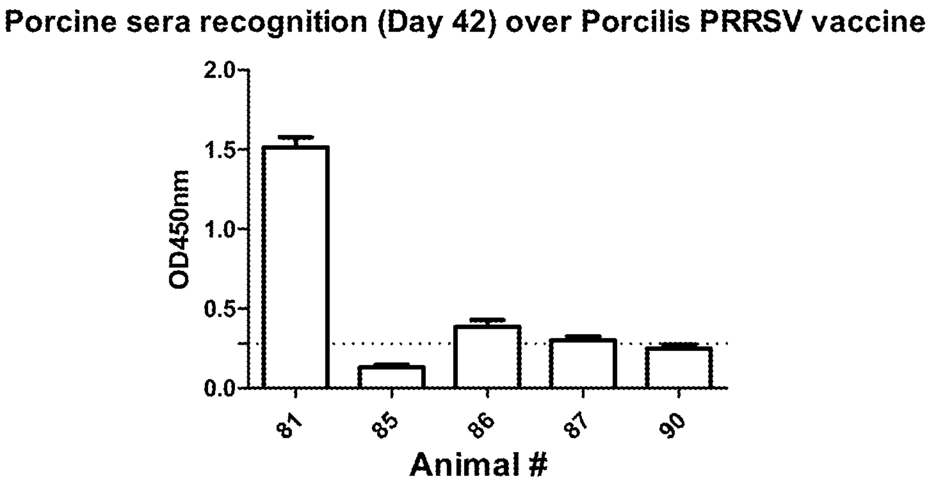
FIG. 6. Porcine sera recognition (Day 42) over Porcilis PRRSV vaccine. Same sera from day 42 of immunization trial was evaluated against attenuated viral particle Porcilis PRRSV (Used as a vaccine for the disease). In the graph samples above dot line are positive for antibodies against this virus (threshold is mean of negative control plus 3 times standard deviation, representing statistical significance $p<0.05$).
Figure 7:
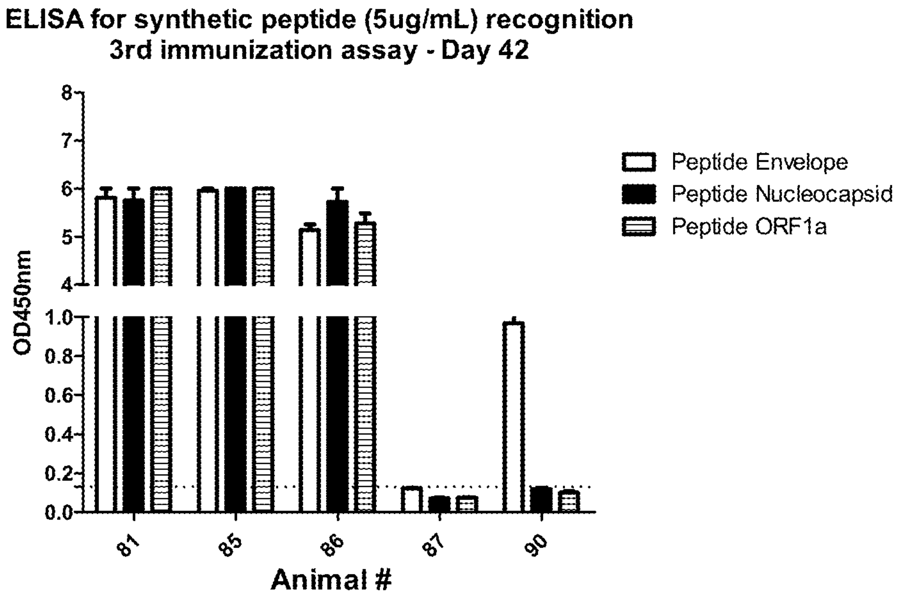
FIG. 7. Porcine sera recognition (Day 42) over synthetic peptides. Same sera from day 42 of immunization trial was evaluated over a three peptide mix (synthetized as shown in this document). In the graph samples above dot line are positive for antibodies against this virus (threshold is mean of negative control plus 3 times standard deviation, representing statistical significance $p<0.05$).

Threshold of positivity was defined as the mean plus three times standard deviation (95% confidence) of the negative control. Threshold for positivity of plates coated with Porcilis was 0.3, and with peptides was 0.13 (FIGS. 6 and 7). Noticeably, sera from animals 81,86,87,88 and 89, which had been vaccinated with peptides or exosomes of the invention, produced antibodies capable of specifically react against Porcilis antigens, validating the capacity of both, peptides and exosomes vaccines, to induce humoral immunity against Porcilis antigens.

Currently, there is a growing demand to consider regional elimination of PRRSV, but that requires reliable vaccines, i.e., those that cannot revert to virulence and spread to nonvaccinates and persist within the swine herds long term. Ideally, the next generation of PRRSV vaccines should also include markers to both differentiate infected from vaccinated animals (DIVA). Remarkably, no antibodies were detected post-vaccination using the IDEXX PRRS X3 Ab test by routine analysis performed in the GSP in any of the animals of this study. This finding reveals that this exosome-based vaccination approach is capable of differentiating infected from vaccinated animals (DIVA).

10.7. Interferon Gamma Production after Vacination.

Sterile white plates for ELISPOT assay (Millipore Cat° S2EM004M99. Lot. R4Ma77120) were activated using 20 μL of 35% Ethanol for 30 seconds. After removing ethanol, plates were washed twice with PBS 1× and coated with 100 μL of Anti-IFNg (BD bioscience—BD559961) at a 1/100 dilution and incubated overnight at 4° C. Coating solutions were discarded and plates were washed with 200 μL of blocking buffer (BB: RPMI 1640 (Lonza, Cat°. BE12-167F)/10% Fetal bovine serum (Life technologies, Cat°. 10270106)/1% L-glutamine (Cultek, Cat°. H3BE17-605E/1% Penicillin/streptomycin (Cultek, cat°. H3DE17-603E). After discarding coating solutions, plates were incubated with BB for 2 hours at room temperature. For stimuli, attenuated viral particles (Pyrsvac-183, SYVA) were resuspended in complete media (CM: RPMI 1640 10% Fetal bovine serum "FBS"/1% L-glutamine/1% Penicillin/streptomycin) to a concentration until normal vaccine dosage in swine, one was loaded into the plate in native conformation and the other denatured by heat at 90° C. for 10 minutes. For peptides, a concentration of 1 μg of each peptide per well (5 μg/mL) diluted in CM was used. Positive control was set as PHA-M at 1/100 dilution and negative control was CM alone. 100 μL of each stimuli were loaded into the plate by duplicate and incubated until cells addition.

Periferal blood mononuclear cells (PBMCs) isolation, whole blood collection was done in EDTA tubes (10 mL approx.—BD Bioscience cat. 366643). Blood was diluted 1:1 with PBS 1× (final volume 20 mL) and loaded above 15 mL of Ficoll Histopaque®-1077 Hybri-Max™ (Sigma, h8889-500ML) in 50 mL Falcon tubes, centrifuged at 1800 rpm/30 minutes at RT AC=9 Dac=3. Collected in 15 mL conical tubes the PBMCs ring at the center of the ficoll gradient with Pasteur pipettes and cells washed twice with PBS1× max volume and centrifuge at 400 g/5 minutes at RT. Cell count and viability was achieved using Flow cytometer and viability assay from BD Pharmigen (PE Annexin V Apoptosis Detection Kit I, Cat 559763) following their own protocol. In cytometer tubes, added 15 μL of cell suspension, 2 μL of 7AAD and 15 μL of calibration beads for cell quantification. Alive cells were counted in a flow cytometer (BD FACSCanto™ II system) and concentration was determined using the following calculations.

Cells/μL=#cells counted/#beads counted (aprox 2000)

Total cell count was determined as follows:

*T*·Cells=cells/μL*2000 μL.

Cell suspension was prepared to load 500000 cells/well and incubated at 37° C. and 5% $CO_2$ for 48 hours. Once finished incubation with stimuli, cells were discarded and plate washed with 200 μL of MiliQ water. Solution was discarded and plate washed three times with PBS 1×/0.05% Tween 20 (PBST). After, 100 μL of Monoclonal antibody Anti-IFNg-Biotine (BD bioscience—BD559958) diluted 1/250 in PBS 1×/10% FBS (PBSS) and incubated for 2 hours at room temperature. Detection antibody solution was discarded and plate washed three times with PBST. 100 μL conjugated Streptavidin-HRPO diluted 1/100 in PBSS was loaded into the plate and incubated for 1 hour at room temperature. Conjugated streptavidin-HRPO solution was discarded and plate washed four times with PBST. Detection was made adding 100 μL of BD ELISPOT AEC substrate set (BD Bioscience Cat. 551951. Lot 4314987) according to manufacturers instructions. Revealing step was stopped using distilled water and then spots were counted (Table 5).

TABLE 5

ELISPOT RESULTS FOR IFN-g PRODUCTION BY PORCINE PBMCs STIMULATION WITH DIFFERENT ANTIGENS.

| Animal # | Pyrsvac-183 (5 × $10^{2-4}$) TCID 50% | 1 μg of each peptide SEQ ID NO: 16, 17 and 18/well |
|---|---|---|
| 81 | 0 | 191 |
| 85 | 43 | 40 |
| 86 | 2 | 37 |
| 87 | 0 | 169.5 |
| 90 | 0 | 184.5 |

The Enzyme-Linked ImmunoSpot (ELISPOT) allows, at appropriate conditions, the visualization of the secretory products of individual activated or responding cells. Each spot that develops in the assay represents a single reactive cell. Thus, the ELISPOT assay provides both qualitative (regarding the specific cytokine or other secreted immune molecule) and quantitative (the frequency of responding cells within the test population) information.

In this particular case, quantification of Interferon gamma (IFN-g) producing cells from the animals vaccinated with peptides or exosomes (Table 4), after stimulation with vaccine antigens or peptides related to PRRSV, was obtained.

The importance of IFN gamma in the immune system stems in part from its ability to inhibit viral replication directly, and most importantly from its immunostimulatory and immunomodulatory effects. IFN gamma is produced predominantly by natural killer (NK) and natural killer T (NKT) cells as part of the innate immune response, and by CD4 Th1 and CD8 cytotoxic T lymphocyte (CTL) effector T cells once antigen-specific immunity develops.

As seen in these results (Table 5), PBMCs derived from animals 81, 85 and 86 vaccinated with the peptides of the invention are able to produce interferon gamma when these cells are subsequently stimulated with these antigens (peptides). Moreover, PBMCs derived from animals 85 (vaccinated with peptide of the invention) produced interferon gamma in the presence of the attenuated viral particle of PRRSV (Pyrsvac-183 vaccine), which was a different antigen than the one used for its vaccination (see Table 4). Most relevant, when animals vaccinated with exosomes from non-viremic animals (87,90) received a single boost with the peptides, these animals produced interfon gamma; thus proving unequivocally that these exosomes contained and exposed such peptides to the immune system of swine. This data shows the capacity of peptides vaccine to induce cellular immunity against PRRSV antigens.

Example 11

11.1. Sample Collection.

Sera samples from farm animals (swine) in which there had been an episode of *Mycoplasma suis* were collected. This farm suffer annual episodes of *Mycoplasma* infections. To determine if these animals were infected by this bacteria, blood samples were analyzed by routine laboratory tests (Zootecnia, Salamanca-Spain), and gave positive results for *Mycoplasma suis* by PCR and microscopy techniques (genus *Mycoplasma*) following their own standard operation procedures.

TABLE 6

ANIMAL SERA INFORMATION FOR VACCINE PREPARATION.

| ID from Farm | Specie | Mycoplasma genus | q-PCR |
|---|---|---|---|
| 200415-MS | Swine | Positive | Positive |
| 200415-RMS | Swine | Positive | Positive |

All these samples were grouped as "cured animals" due to the fact that samples received at Innovex Therapeutics were collected after the disease and clinical symptoms disappeared of the population.

11.2. Serum-Derived Exosome Isolation.

The exosomes have a characteristic particle size of 30-100 nm. Therefore, to collect these vesicles from different samples a separation process through size exclusion chromatography using sepharose CL2B as separation matrix, was used (Boing A. N. et al., "Single-step isolation of extracellular vesicles by size-exclusion chromatography", 2014, J. Extracell Vesicles, 3). While there are other techniques for preparing exosomes, the sepharose technique allows a better purification of the exosomes. Briefly, frozen 3 mL aliquots of different sera samples were thawed on ice and centrifuged at 500 g for 10 minutes at room temperature to disrcard cell debris. In parallel, sepharose CL-2B (Sigma-Aldrich, St. Louis, Mo., USA) were packed in 12 mL syringes until a final volume of 10 mL, and balanced with phosphate-buffered saline (PBS) 0.32% of sodium citrate (w/v). Later, 2 mL aliquots of each sample were added to individual sepharose CL-2B columns and 18-20 fractions of 0.5 mL aliquots were collected for each sample.

11.3. Molecular Characterization of Exosomes.

Once obtained the different exosome fractions, the presence of the vesicles was confirmed by the analysis of protein concentration using Bradford assay, and the analysis using molecular markers performed by flow cytometry.

11.3.1. Bradford Analysis.

Protein concentration was obtained using a colorimetric assay with Bradford technique (Bradford M. M. "A rapid and sensitive method for the quantitation of microgram quantities of protein utilizing the principle of protein-dye binding", 1976, Analytical biochemistry, vol. 7(72), páginas 248-254)

11.3.2. Flow Cytometry.

In parallel, fractions were also analyzed by flow cytometry to detect the presence of the antigens CD9, CD63 or CD81, three tetraspanins that are particular exosome markers (Raposo G. et al., "Extracellular vesicles: exosomes, microvesicles, and friends", 2013, The Journal of cell biology, vol. 18(200), page 373-383). Each aliquot was subjected to the following protocol: 4 microns of latex beads (aldehyde-sulfate) (Invitrogen Cat° A37304) were added to each aliquot, and the mix was left for 15 minutes in resting conditions before adding 1 mL of BCB buffer (PBS 1×, 0.1% bovine serum albumin, 0.01% sodium azide). The resulting mix was incubated overnight at room temperature in rotation before the incubation with primary antibodies (anti-CD63, anti-CD9 and anti-CD81, kindly provided by Dr. Francisco Sanchez-Madrid) for 30 minutes at 4° C. Both antibodies were used in 1:10 dilution. After two wash steps with 150 μL of PBS-BSA buffer (Phosphate-buffered saline/bovine serum albumin 0.1%), and centrifugation at 2000 g for 10 minutes, secondary antibodies conjugated to FITC (1:100 dilution) or alexa 488 (1:1000 dillution) (Southern Biotec cat° 1032-02) were added and the mix was incubated for 30 minutes at 4° C. After two additional wash steps with 150 μL of PBS-BSA buffer at 0.1% at 2000 g for 10 minutes, the latex beads were resuspended in 100 μL of PBS-BSA 0.1%.

Resulting samples were analyzed by flow cytometry using LRSFortessa flow cytometer (BD Biosciences) and adjusting counting threshold at 10000 events. Using FlowJo analysis software, FCS files corresponding to each sample processed were added to the worklist, the area (forward and side scatter) where latex beads population was concentrated, was selected, and the fluorescence for FITC related to this area was measured. A table was made with the median intensity fluorescence (MFI) data and bead counts obtained in the gated area for each sample analyzed. 20000 individual latex beads were examined per sample and the MFI was used for comparison between fractions.

Figure 8:
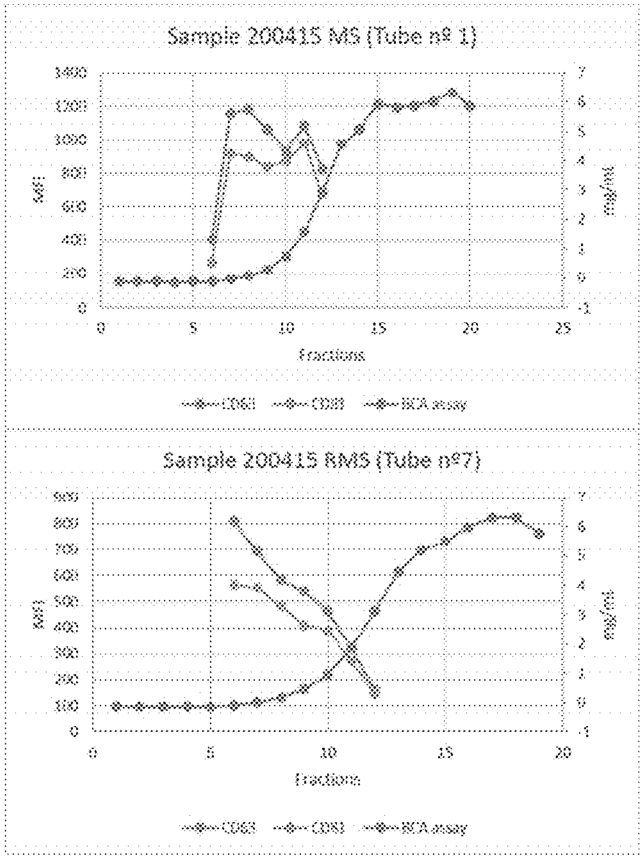
FIG. 8. Characterization of exosomes derived from swine sera (animals cured from *Mycoplasma* infection). In the samples, a mix of fractions enriched in exosomes (fractions 6 to 9) were selected as the ones with the highest concentration of exosomes and to be further analyzed. CD63 and CD81 are used as guide for selecting fractions to be send to proteomic analyses.

Following both protocols, as shown in FIG. 8, it was possible to identify the exosome containing fractions from those containing soluble protein, verifying, additionally, that viremic and non-viremic samples had a similar elution pattern: it was detected an increase in fluorescence signal for CD63 and CD81 molecular markers just before Bradford analysis started to detect soluble protein in analyzed fractions.

11.4. Exosome Protein Profile Analysis.

11.4.1. Analysis of the Distribution and Size of the Exosomes Using Nanoparticle Tracking Analysis (NTA).

The use of NTA for quantification, distribution and size of microvesicles, particularly exosomes, has become one of the most used techniques in the extracellular vesicles field. (malvern.com/en/products/technoloy/nano-particle-tracking-analysis/). Therefore, after the confirmation of the presence of the markers associated to these vesicles in the fractions, we decided to quantify the number and the size of the microvesicles population present in the analyzed samples. In order to do so, each analyzed sample was diluted in PBS until the NTA chamber (Malvern Instru-ments Ltd) detected a value between 20-100 particles per field. Once reached this ideal concentration and dilution, 400 μL were injected into the NTA chamber and microscope capture level was manually adjusted. The digital thermometer was activated and the focalization of the particles with less refraction was started using the micrometer of the microscope in the area closest to the laser beam circumferences. Automatic acquisition of videos was started, and the analysis of the obtained videos was done using the software developed by the equipment's supplier. Thus, it was confirmed that the majority of samples had a vesicle concentration in order of magnitude of 1010 particles per milliliter. In addition, mode size was measured and ranged between 40-150 nm.

11.5. Proteomic Analysis Using Liquid Chromatography and Mass Spectrometry.

Liquid chromatography (nanoLCULTRA-EKSIGENT) followed by mass spectrometry (LC-MS/MS) was carried out in an LTQ Orbitrap Velos equipment (Thermo Fisher). Exosome samples in PBS, were reduced with 10 mM DTT (Dithiothreitol), alkylated with 55 mM of iodoacetamide, and precipitated with 10% trichloroacetic acid (TCA), washed with 100% acetone and reconstituted in 2 mL of 8M urea. Before overnight digestion with trypsin, samples were resuspended in 1.6M urea solution. Reaction was stopped with 1% formic acid (v/v) and trypsinized samples were passed through a precolumn (C18PepMap-100-Thermoscientific-5 mm-ID300 um-5 um-100 A), before their injection in an analytical column (AcclaimPepMap100-Thermoscientific-15 cm-ID75 um-3 um-100 A-C18). Samples eluted at 400 nL/minute with a mobile phase gradient: 0-40% of dissolvent B in dissolvent A for the first 80-90 minutes and then 40-100% of dissolvent B in dissolvent A until experiment ending at 100-110 minutes (A: 3% acetonitrile, 0.1% formic acid in water, B: 97% acetonitrile, 0.1% formic acid in water). The Eluate was applied to the nano-spray source of the spectrometer Orbitrap and all full-scan mass spectra acquired in the Orbitrap over a mass range of 400-1500 m/z with a resolution of 30,000 and a maximum injection time of 500 ms were analyzed. The MS/MS was done in the LTQ and the 20 more intense peptides were isolated and fragmented using a low collision energy 35% CID. Maxquant v1.5 software was used to analyze the raw data, using the label-free-quantification (LFQ) mode. Moreover, for the final identification we used the sequence search engine, Andromeda (module included in Maxquant v1.5 software), adding a sequence dataset created from the sequences obtained from the UniProtKB website, including all *Mycoplasma suis* proteins sequences that had been sequenced until that moment (approximately 4566 sequences).

TABLE 7

BACTERIAL PROTEINS IDENTIFIED BY LC-MS/MS.

| SEQ ID NO | Sequence | Protein |
|---|---|---|
| 6 | LEELFK | ABC transporter ATP-binding protein |
| 7 | KGSIVDIENQK | tRNA(5-methylaminomethyl-2-thiouridine)-methyltransferase |

From this analysis, two bacterial proteins were identified and two of them with more than two unique peptides. Thus, it could be concluded that exosomes produced in an animal (Swine), which has overcome the disease (Mycoplasmosis), and that does not present traces of the pathogen, expresses the proteins shown in the table below. Importantly, all proteins identified by Maxquant v1.5 have an associated probability known as PEP or posterior error probability, which indicates the probability to misidentify one protein by comparison. All the proteins identified in this analysis presented a PEP<0.0001, reinforcing the validity of these results.

Example 12

12.1. Sample Collection.

Sera samples from farm animals (Frisona Bovine strain) in which there had been an episode of *Theileriosis* were collected. This farm suffer annual episodes of *Theileriosis* (endemic of Menorca Island). The episode occurred between October and December of 2015. To determine if these animals were infected by this parasite, blood samples were analyzed by routine laboratory tests (Menorca), and gave positive (moderate-high) results for *Theileria* sp. Most of the tested animals died after laboratory diagnosis and presented symptoms like high fever, jaundice, anorexy, prostration and loss of milk in lactating cows.

All these samples were grouped as "cured animals" due to the fact that survive the disease after treatment.

TABLE 8

ANIMAL SERA INFORMATION FOR VACCINE PREPARATION.

| ID from Farm | Specie | Strain | Location | Affected in | Age (yrs) | Lactancy |
|---|---|---|---|---|---|---|
| 7534 | Bovine | Frisona | Menorca | October-December | 2 | N/A |
| 6888 | Bovine | Frisona | Menorca | October-December | 2 | N/A |

12.2. Serum-Derived Exosome Isolation.

The exosomes have a characteristic particle size of 30-100 nm. Therefore, to collect these vesicles from different samples a separation process through size exclusion chromatography using sepharose CL2B as separation matrix, was used (Boing A. N. et al., "Single-step isolation of extracellular vesicles by size-exclusion chromatography", 2014, J. Extracell Vesicles, 3). While there are other techniques for preparing exosomes, the sepharose technique allows a better purification of the exosomes. Briefly, frozen 3 mL aliquots of different sera samples were thawed on ice and centrifuged at 500 g for 10 minutes at room temperature to discard cell debris. In parallel, sepharose CL-2B (Sigma-Aldrich, St. Louis, Mo., USA) were packed in 12 mL syringes until a final volume of 10 mL, and balanced with phosphate-buffered saline (PBS) 0.32% of sodium citrate (w/v). Later, 2 mL aliquots of each sample were added to individual sepharose CL-2B columns and 18-20 fractions of 0.5 mL aliquots were collected for each sample.

12.3. Molecular Characterization of Exosomes.

Once obtained the different exosome fractions, the presence of the vesicles was confirmed by the analysis of protein concentration using Bradford assay, and the analysis using molecular markers performed by flow cytometry.

12.3.1. Bradford Analysis.

Protein concentration was obtained using a colorimetric assay with Bradford technique (Bradford M. M. "A rapid and sensitive method for the quantitation of microgram quantities of protein utilizing the principle of protein-dye binding", 1976, Analytical biochemistry, vol. 7(72), páginas 248-254)

12.3.2. Flow Cytometry.

In parallel, fractions were also analyzed by flow cytometry to detect the presence of the antigens CD63 or CD81, two tetraspanins that are particular exosome markers (Raposo G. et al., "Extracellular vesicles: exosomes, microvesicles, and friends", 2013, The Journal of cell biology, vol. 18(200), page 373-383). Each aliquot was subjected to the following protocol: 4 microns of latex beads (aldehyde-sulfate) (Invitrogen Cat° A37304) were added to each aliquot, and the mix was left for 15 minutes in resting conditions before adding 1 mL of BCB buffer (PBS 1×, 0.1% Bovine serum albumin, 0.01% Sodium azide). The resulting mix was incubated overnight at room temperature in rotation before the incubation with primary antibodies (anti-CD63 and anti-CD81, kindly provided by Dr. Francisco Sanchez-Madrid) for 30 minutes at 4° C. Both antibodies were used in 1:10 dilution. After two wash steps with 150 μL of PBS-BSA buffer (Phosphate-buffered saline/bovine serum albumin 0.1%), and centrifugation at 2000 g for 10 minutes, secondary antibodies conjugated to FITC (1:100 dilution) or alexa 488 (1:1000 dillution) (Southern Biotec cat° 1032-02) were added and the mix was incubated for 30 minutes at 4° C. After two additional wash steps with 150 μL of PBS-BSA buffer at 0.1% at 2000 g for 10 minutes, the latex beads were resuspended in 100 μL of PBS-BSA 0.1%.

Resulting samples were analyzed by flow cytometry using LRSFortessa flow cytometer (BD Biosciences) and adjusting counting threshold at 10000 events. Using FlowJo analysis software, FCS files corresponding to each sample processed were added to the worklist, the area (forward and side scatter) where latex beads population was concentrated, was selected, and the fluorescence for FITC related to this area was measured. A table was made with the median intensity fluorescence (MFI) data and bead counts obtained in the gated area for each sample analyzed. 20000 individual latex beads were examined per sample and the MFI was used for comparison between fractions.

Figure 9:
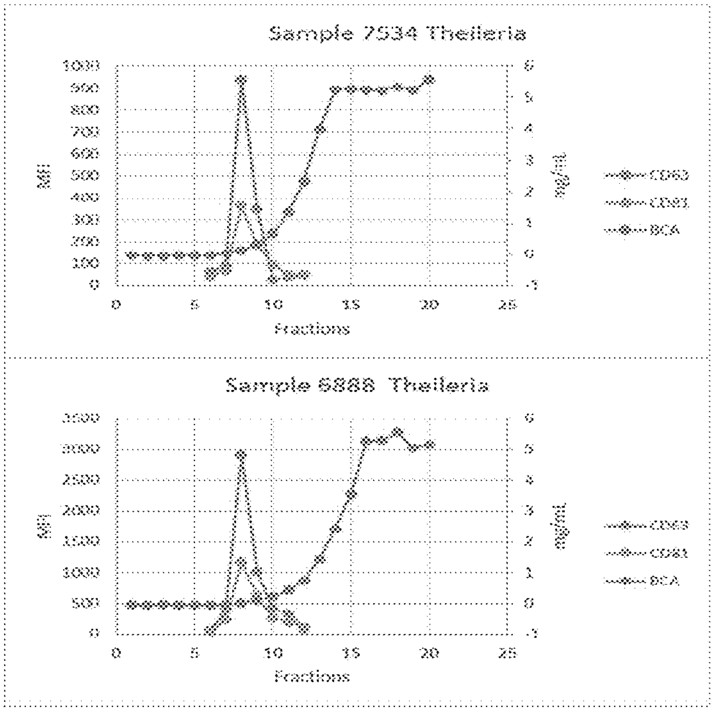
FIG. 9. Characterization of exosomes derived from non-parasitic bovine sera.

Following both protocols, as shown in FIG. 9, it was possible to identify the exosome containing fractions from those containing soluble protein, verifying, additionally, that viremic and non-viremic samples had a similar elution pattern: it was detected an increase in fluorescence signal for CD63 and CD81 molecular markers just before Bradford analysis started to detect soluble protein in analyzed fractions.

12.4. Exosome Protein Profile Analysis.

12.4.1. Analysis of the Distribution and Size of the Exosomes Using Nanoparticle Tracking Analysis (NTA).

The use of NTA for quantification, distribution and size of microvesicles, particularly exosomes, has become one of the most used techniques in the extracellular vesicles field. (malvern.com/en/products/technolov/nanoarticle-tracking-analysis/). Therefore, after the confirmation of the presence of the markers associated to these vesicles in the fractions, we decided to quantify the number and the size of the microvesicles population present in the analyzed samples. In order to do so, each analyzed sample was diluted in PBS until the NTA chamber (Malvern Instruments Ltd) detected a value between 20-100 particles per field. Once reached this ideal concentration and dilution, 400 μL were injected into the NTA chamber and microscope capture level was manually adjusted. The digital thermometer was activated and the focalization of the particles with less refraction was started using the micrometer of the microscope in the area closest to the laser beam circumferences. Automatic acquisition of videos was started, and the analysis of the obtained videos was done using the software developed by the equipment's supplier. Thus, it was confirmed that the majority of samples had a vesicle concentration in order of magnitude of 1010 particles per milliliter. In addition, mode size was measured and ranged between 40-150 nm.

12.5. Proteomic Analysis Using Liquid Chromatography and Mass Spectrometry.

Liquid chromatography (nanoLCULTRA-EKSIGENT) followed by mass spectrometry (LC-MS/MS) was carried out in an LTQ Orbitrap Velos equipment (Thermo Fisher). Exosome samples in PBS, were reduced with 10 mM DTT (Dithiothreitol), alkylated with 55 mM of iodoacetamide, and precipitated with 10% trichloroacetic acid (TCA), washed with 100% acetone and reconstituted in 2 mL of 8M urea. Before overnight digestion with trypsin, samples were resuspended in 1.6M urea solution. Reaction was stopped with 1% formic acid (v/v) and trypsinized samples were passed through a precolumn (C18PepMap-100-Thermoscientific-5 mm-ID300 um-5 um-100 A), before their injection in an analytical column (AcclaimPepMap100-Thermoscientific-15 cm-ID75 um-3 um-100 A-C18). Samples eluted at 400 nL/minute with a mobile phase gradient: 0-40% of dissolvent B in dissolvent A for the first 80-90 minutes and then 40-100% of dissolvent B in dissolvent A until experiment ending at 100-110 minutes (A: 3% acetonitrile, 0.1% formic acid in water, B: 97% acetonitrile, 0.1% formic acid in water). The Eluate was applied to the nano-spray source of the spectrometer Orbitrap and all full-scan mass spectra acquired in the Orbitrap over a mass range of 400-1500 m/z with a resolution of 30,000 and a maximum injection time of 500 ms were analyzed. The MS/MS was done in the LTQ and the 20 more intense peptides were isolated and fragmented using a low collision energy 35% CID. Maxquant v1.5 software was used to analyze the raw data, using the label-free-quantification (LFQ) mode. Moreover, for the final identification we used the sequence search engine, Andromeda (module included in Maxquant v1.5 software), adding a sequence dataset created from the sequences obtained from the UniProtKB website, including all *Theileria* sp. proteins sequences that had been sequenced until that moment (approximately 18779 sequences).

From this analysis, five parasite proteins were identified and two of them with more than two unique peptides. Thus, it could be concluded that exosomes produced in an animal (Bovine), which has overcome the disease (*Theileriosis*), and that does not present traces of the pathogen, expresses the proteins show in the table below. Importantly, all proteins identified by Maxquant v1.5 have an associated probability known as PEP or posterior error probability, which indicates the probability to misidentify one protein by comparison. All the proteins identified in this analysis presented a PEP<0.0001, reinforcing the validity of these results.

TABLE 9

PARASITE PROTEINS IDENTIFIED BY LC-MS/MS.

| SEQ ID No: | Sequence |
|---|---|
| 8 | MQIFVK |
| 9 | TITLEVEPSDTIENVK |
| 10 | IENLSDTFLSNNGKPEYKR |
| 11 | AGFAGDDAPR |
| 12 | IWHHTFYNELR |
| 13 | YPIEHGIVTNWEDMEK |
| 14 | STELLIRK |
| 15 | EGDGVCTITAKMPKDEQK |

The invention claimed is:

1. A Porcine Reproductive and Respiratory Syndrome Virus (PRRSV) free immunogenic pharmaceutical or veterinary composition comprising:

an enriched fraction of immunogenic exosomes having immunogenic pathogenic peptides on its surface, wherein:

the exosomes are isolated from a biological fluid sample of a non-viremic swine which (a) has overcome a respiratory disease caused by a PRRSV, and (b) it is free from the PRRSV that causes the disease, wherein the features (a) and (b) are determined in the body fluid sample of the swine by performing RT-PCR and detecting PRRSV antibodies, wherein the swine has overcome the disease and it is free from the pathogen when it is RT-PCR negative and antibodies for PRRSV are detected; wherein the exosome comprises a peptide comprising a sequence selected from the group consisting of SEQ ID NO: 1 to SEQ ID NO: 5, and a peptide with an identity sequence of at least 85% with any of the sequences SEQ ID NO: 1 to 5; and wherein the pathogen-free immunogenic pharmaceutical or veterinary composition comprises one or more pharmaceutically or veterinary acceptable adjuvants and one or more pharmaceutically or veterinary acceptable excipients or carriers.

2. The immunogenic composition according to claim 1, wherein the swine is a farm swine.

3. The immunogenic composition according to claim 1, wherein the exosome comprises the peptides SEQ ID NO:1 to SEQ ID NO: 5.

4. The immunogenic composition according to claim 3, wherein the exosome comprises one peptide of sequence SEQ ID NO: 16, 17, and 18, or a sequence having at least 85% of identity with any of the sequences SEQ ID NO: 16 to 18.

5. The immunogenic composition according to claim 4, wherein the exosome comprises a peptide of sequence SEQ ID NO: 16, 17, or 18.

6. The immunogenic composition according to claim 4, wherein the exosome comprises the peptides of sequence SEQ ID NO: 16, 17, and 18.

7. A process for obtaining the PRRSV free immunogenic composition as defined in claim 1 that comprises: (i) obtaining an enriched fraction of immunogenic exosomes from an isolated biological fluid-sample of non-viremic swine that (a) has overcome a respiratory disease caused by PRRSV, and (b) it is free from the PRRSV that causes the disease, as it is defined in any of the previous claims; and (ii) the mixture of the exosomes resulting from step (i) with one or more pharmaceutically or veterinary acceptable excipients or carriers and one or more pharmaceutically or veterinary acceptable adjuvants; wherein the features (a) and (b) are determined in the body fluid sample of the swine by performing RT-PCR and detecting PRRSV antibodies, wherein the swine has overcome the disease and it is free from the pathogen when it is RT-PCR negative and antibodies for PRRSV are detected wherein the exosome comprises a peptide comprising a sequence selected from the group consisting of SEQ ID NO: 1 to SEQ ID NO: 5, and a peptide with an identity sequence of at least 85% with any of the sequences SEQ ID NO: 1 to 5.

8. The process according to claim 7, wherein the isolated sample is a serum sample.

9. The process according to claim 7, wherein the exosomes are separated using size exclusion chromatography.

10. The process according to claim 7, wherein the isolated sample is serum and the exosomes are separated using size exclusion chromatography.

11. The immunogenic composition according to claim 1, which is a vaccine.

12. A method for the treatment or prevention of a PRRSV disease, the method comprising administering a therapeutically effective amount of the immunogenic composition as defined in claim 1, in a subject in need thereof.

13. A method for identifying a peptide candidate to be an immunogen, the method comprising the step of analyzing the protein composition of an exosome as defined in claim 1.

14. A method for differentiating animals vaccinated with the exosome as defined in claim 1 from the animals infected with the same pathogen as the one referred in claim 1, the method comprising determining the antibody profile in an animal's isolated sample and comparing it with a reference antibody profile from an already vaccinated animal or from an infected animal, wherein if the antibody profile from the isolated sample is substantially the same as the one from the vaccinated animal reference, this will be indicative that the test animal is vaccinated with the immunogenic composition as defined in claim 1, and if the antibody profile from the isolated sample is substantially the same as the one from the infected animal reference, this will be indicative that the test animal is infected.

15. A method for increasing imunogenicity against a PRRSV disease, the method comprising administering a therapeutically effective amount of the immunogenic composition as defined in claim 1, in a subject in need thereof.

16. The PRRSV-free immunogenic composition according to claim 1, wherein the exosome in addition comprises the cysteine-protease clab/similar to papain, PRRSV uncharacterized putative protein, PRRSV polyprotein, NSP2, GP2b and ORF2a proteins.

* * * * *

SEQUENCE LISTING

```
<160> NUMBER OF SEQ ID NOS: 18

<210> SEQ ID NO 1
<211> LENGTH: 11
<212> TYPE: PRT
<213> ORGANISM: Artificial Sequence
<220> FEATURE:
<223> OTHER INFORMATION: peptide

<400> SEQUENCE: 1

Val Glu Val Glu Gly His Leu Met Thr Ser Lys
1               5                   10


<210> SEQ ID NO 2
<211> LENGTH: 12
<212> TYPE: PRT
<213> ORGANISM: Artificial Sequence
<220> FEATURE:
<223> OTHER INFORMATION: peptide

<400> SEQUENCE: 2

Gln Ala Lys Lys His Glu Val Ala Gly Ala Asn Lys
1               5                   10
```

-continued

```
<210> SEQ ID NO 3
<211> LENGTH: 8
<212> TYPE: PRT
<213> ORGANISM: Artificial Sequence
<220> FEATURE:
<223> OTHER INFORMATION: peptide

<400> SEQUENCE: 3

Ala Gly Lys Lys Gln Ser Gln Lys
1               5


<210> SEQ ID NO 4
<211> LENGTH: 23
<212> TYPE: PRT
<213> ORGANISM: Artificial Sequence
<220> FEATURE:
<223> OTHER INFORMATION: peptide

<400> SEQUENCE: 4

Asn Ile Ala Pro Met Gly Asn Gly Gln Ser Val Asn Gln Leu Cys Gln
1               5                   10                  15

Leu Leu Gly Thr Met Met Lys
            20


<210> SEQ ID NO 5
<211> LENGTH: 9
<212> TYPE: PRT
<213> ORGANISM: Artificial Sequence
<220> FEATURE:
<223> OTHER INFORMATION: peptide

<400> SEQUENCE: 5

Met Ala Gly Arg Asn Gln Arg Gln Lys
1               5


<210> SEQ ID NO 6
<211> LENGTH: 6
<212> TYPE: PRT
<213> ORGANISM: Artificial Sequence
<220> FEATURE:
<223> OTHER INFORMATION: peptide

<400> SEQUENCE: 6

Leu Glu Glu Leu Phe Lys
1               5


<210> SEQ ID NO 7
<211> LENGTH: 11
<212> TYPE: PRT
<213> ORGANISM: Artificial Sequence
<220> FEATURE:
<223> OTHER INFORMATION: peptide

<400> SEQUENCE: 7

Lys Gly Ser Ile Val Asp Ile Glu Asn Gln Lys
1               5                   10


<210> SEQ ID NO 8
<211> LENGTH: 6
<212> TYPE: PRT
<213> ORGANISM: Artificial Sequence
<220> FEATURE:
<223> OTHER INFORMATION: peptide

<400> SEQUENCE: 8
```

Met Gln Ile Phe Val Lys
1 5

<210> SEQ ID NO 9
<211> LENGTH: 16
<212> TYPE: PRT
<213> ORGANISM: Artificial Sequence
<220> FEATURE:
<223> OTHER INFORMATION: peptide

<400> SEQUENCE: 9

Thr Ile Thr Leu Glu Val Glu Pro Ser Asp Thr Ile Glu Asn Val Lys
1 5 10 15

<210> SEQ ID NO 10
<211> LENGTH: 19
<212> TYPE: PRT
<213> ORGANISM: Artificial Sequence
<220> FEATURE:
<223> OTHER INFORMATION: peptide

<400> SEQUENCE: 10

Ile Glu Asn Leu Ser Asp Thr Phe Leu Ser Asn Asn Gly Lys Pro Glu
1 5 10 15

Tyr Lys Arg

<210> SEQ ID NO 11
<211> LENGTH: 10
<212> TYPE: PRT
<213> ORGANISM: Artificial Sequence
<220> FEATURE:
<223> OTHER INFORMATION: peptide

<400> SEQUENCE: 11

Ala Gly Phe Ala Gly Asp Asp Ala Pro Arg
1 5 10

<210> SEQ ID NO 12
<211> LENGTH: 11
<212> TYPE: PRT
<213> ORGANISM: Artificial Sequence
<220> FEATURE:
<223> OTHER INFORMATION: peptide

<400> SEQUENCE: 12

Ile Trp His His Thr Phe Tyr Asn Glu Leu Arg
1 5 10

<210> SEQ ID NO 13
<211> LENGTH: 16
<212> TYPE: PRT
<213> ORGANISM: Artificial Sequence
<220> FEATURE:
<223> OTHER INFORMATION: peptide

<400> SEQUENCE: 13

Tyr Pro Ile Glu His Gly Ile Val Thr Asn Trp Glu Asp Met Glu Lys
1 5 10 15

<210> SEQ ID NO 14
<211> LENGTH: 8
<212> TYPE: PRT
<213> ORGANISM: Artificial Sequence
<220> FEATURE:
<223> OTHER INFORMATION: peptide

<400> SEQUENCE: 14

```
Ser Thr Glu Leu Leu Ile Arg Lys
1               5


<210> SEQ ID NO 15
<211> LENGTH: 18
<212> TYPE: PRT
<213> ORGANISM: Artificial Sequence
<220> FEATURE:
<223> OTHER INFORMATION: peptide

<400> SEQUENCE: 15

Glu Gly Asp Gly Val Cys Thr Ile Thr Ala Lys Met Pro Lys Asp Glu
1               5                   10                  15

Gln Lys


<210> SEQ ID NO 16
<211> LENGTH: 35
<212> TYPE: PRT
<213> ORGANISM: Artificial Sequence
<220> FEATURE:
<223> OTHER INFORMATION: peptide

<400> SEQUENCE: 16

Leu Asp Ala Lys Gly Arg Leu Tyr Arg Trp Arg Ser Pro Val Ile Ile
1               5                   10                  15

Glu Lys Gly Gly Lys Val Glu Val Glu Gly His Leu Met Thr Ser Lys
            20                  25                  30

Glu Leu Cys
        35


<210> SEQ ID NO 17
<211> LENGTH: 35
<212> TYPE: PRT
<213> ORGANISM: Artificial Sequence
<220> FEATURE:
<223> OTHER INFORMATION: peptide

<400> SEQUENCE: 17

Gln Ala Lys Lys His Glu Val Ala Gly Ala Asn Lys Ala Glu His Leu
1               5                   10                  15

Lys His Tyr Ser Pro Pro Ala Glu Gly Asn Cys Gly Trp His Cys Ile
            20                  25                  30

Ser Ala Ile
        35


<210> SEQ ID NO 18
<211> LENGTH: 35
<212> TYPE: PRT
<213> ORGANISM: Artificial Sequence
<220> FEATURE:
<223> OTHER INFORMATION: peptide

<400> SEQUENCE: 18

Met Ala Gly Arg Asn Gln Ser Gln Lys Lys Lys Lys Asn Ile Ala Pro
1               5                   10                  15

Met Gly Asn Gly Gln Ser Val Asn Gln Leu Cys Gln Leu Leu Gly Thr
            20                  25                  30

Met Met Lys
        35
```